US010149607B2

(12) United States Patent
Choset et al.

(10) Patent No.: US 10,149,607 B2
(45) Date of Patent: Dec. 11, 2018

(54) STEERABLE, FOLLOW THE LEADER DEVICE

(71) Applicants:CARNEGIE MELLON UNIVERSITY, Pittsburgh, PA (US); UNIVERSITY OF PITTSBURGH—OF THE COMMONWEALTH SYSTEM OF HIGHER EDUCATION, Pittsburgh, PA (US)

(72) Inventors: Howard M. Choset, Pittsburgh, PA (US); Alon Wolf, Haifa (IL); Marco A. Zenati, Pittsburgh, PA (US)

(73) Assignees: Carnegie Mellon University, Pittsburgh, PA (US); University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/584,136

(22) Filed: Dec. 29, 2014

(65) Prior Publication Data

US 2015/0164491 A1 Jun. 18, 2015

Related U.S. Application Data

(62) Division of application No. 11/630,279, filed as application No. PCT/US2005/022442 on Jun. 24, 2005, now Pat. No. 9,011,318.
(Continued)

(51) Int. Cl.
*A61B 1/00* (2006.01)
*A61B 1/005* (2006.01)
(Continued)

(52) U.S. Cl.
CPC ........ *A61B 1/0055* (2013.01); *A61B 1/00006* (2013.01); *A61B 1/008* (2013.01);
(Continued)

(58) Field of Classification Search
USPC .......................... 600/114, 121–125, 139–144
See application file for complete search history.

(56) References Cited

U.S. PATENT DOCUMENTS 3,060,972 A 10/1962 Sheldon
3,643,653 A 2/1972 Takahashi et al.
(Continued)

FOREIGN PATENT DOCUMENTS

JP          S6048294 A      3/1985
WO    WO-2003073920 A2    9/2003
(Continued)

OTHER PUBLICATIONS

Shammas et al., "New Joint Design for Three-dimensional Hyper Redundant Robots," International Conference on Robots and Systems, Las Vegas, NV, Oct. 2003.
(Continued)

*Primary Examiner* — Matthew J Kasztejna
(74) *Attorney, Agent, or Firm* — Fox Rothschild LLP

(57) ABSTRACT

A highly articulated robotic probe (HARP) is comprised of a first mechanism and a second mechanism, one or both of which can be steered in desired directions. Each mechanism can alternate between being rigid and limp. In limp mode the mechanism is highly flexible. When one mechanism is limp, the other is rigid. The limp mechanism is then pushed or pulled along the rigid mechanism. The limp mechanism is made rigid, thereby assuming the shape of the rigid mechanism. The rigid mechanism is made limp and the process repeats. These innovations allow the device to drive anywhere in three dimensions. The device can "remember" its
(Continued)

previous configurations, and can go anywhere in a body or other structure (e.g. jet engine). When used in medical applications, once the device arrives at a desired location, the inner core mechanism can be removed and another functional device such as a scalpel, clamp or other tool slid through the rigid sleeve to perform. Because of the rules governing abstracts, this abstract should not be used to construe the claims.

19 Claims, 22 Drawing Sheets

Related U.S. Application Data

(60) Provisional application No. 60/583,094, filed on Jun. 25, 2004.

(51) Int. Cl.
| | | |
|---|---|---|
| *A61B 1/05* | (2006.01) | |
| *A61B 17/00* | (2006.01) | |
| *A61B 90/10* | (2016.01) | |
| *A61B 34/00* | (2016.01) | |
| *A61B 34/30* | (2016.01) | |
| *A61B 1/008* | (2006.01) | |
| *A61B 1/31* | (2006.01) | |
| *A61B 17/34* | (2006.01) | |
| *A61B 34/20* | (2016.01) | |
| *A61B 90/00* | (2016.01) | |
| *A61B 90/11* | (2016.01) | |

(52) U.S. Cl.
CPC .......... *A61B 1/0016* (2013.01); *A61B 1/0052* (2013.01); *A61B 1/0053* (2013.01); *A61B 1/05* (2013.01); *A61B 1/31* (2013.01); *A61B 17/00234* (2013.01); *A61B 34/20* (2016.02); *A61B 34/30* (2016.02); *A61B 34/70* (2016.02); *A61B 90/10* (2016.02); *A61B 90/11* (2016.02); *A61B 2017/00314* (2013.01); *A61B 2017/00327* (2013.01); *A61B 2017/00336* (2013.01); *A61B 2017/3445* (2013.01); *A61B 2034/2063* (2016.02); *A61B 2034/301* (2016.02); *A61B 2090/374* (2016.02); *A61B 2090/376* (2016.02); *A61B 2090/378* (2016.02)

(56) References Cited

U.S. PATENT DOCUMENTS

| 4,941,455 A | 7/1990 | Watanabe et al. |
|---|---|---|
| 5,143,475 A | 9/1992 | Chikama |
| 5,174,276 A * | 12/1992 | Crockard ............ A61B 17/1285 600/104 |
| 5,251,611 A | 10/1993 | Zehel et al. |
| 5,318,526 A | 6/1994 | Cohen |
| 5,327,905 A | 7/1994 | Avitall |
| 5,386,741 A | 2/1995 | Rennex |
| 5,467,763 A | 11/1995 | McMahon et al. |
| 5,472,017 A | 12/1995 | Kovalcheck |
| 5,483,951 A | 1/1996 | Frassica et al. |
| 5,514,157 A | 5/1996 | Nicholas et al. |
| 5,531,715 A | 7/1996 | Engelson et al. |
| 5,549,542 A | 8/1996 | Kovalcheck |
| 5,605,543 A | 2/1997 | Swanson |
| 5,662,587 A | 9/1997 | Grundfest et al. |
| 5,743,876 A | 4/1998 | Swanson |
| 5,759,151 A | 6/1998 | Sturges |
| 6,036,677 A | 3/2000 | Javier, Jr. et al. |
| 6,197,017 B1 | 3/2001 | Brock et al. |
| 6,221,061 B1 | 4/2001 | Engelson et al. |
| 6,270,453 B1 | 8/2001 | Sakai |
| 6,432,112 B2 | 8/2002 | Brock et al. |
| 6,517,477 B1 | 2/2003 | Wendlandt |
| 6,554,844 B2 | 4/2003 | Lee et al. |
| 6,610,007 B2 | 8/2003 | Belson et al. |
| 6,623,448 B2 | 9/2003 | Slater |
| 6,638,266 B2 | 10/2003 | Wilson et al. |
| 6,682,493 B2 | 1/2004 | Mirigian |
| 6,692,485 B1 | 2/2004 | Brock et al. |
| 6,697,048 B2 | 2/2004 | Rosenberg et al. |
| 6,730,020 B2 | 5/2004 | Peng et al. |
| 6,790,173 B2 | 9/2004 | Saadat et al. |
| 6,800,056 B2 | 10/2004 | Tartaglia et al. |
| 6,827,710 B1 | 12/2004 | Mooney et al. |
| 6,837,847 B2 | 1/2005 | Ewers et al. |
| 6,858,005 B2 | 2/2005 | Ohline et al. |
| 6,869,396 B2 | 3/2005 | Belson |
| 6,890,297 B2 | 5/2005 | Belson |
| 6,899,673 B2 | 5/2005 | Ogura et al. |
| 6,907,298 B2 | 6/2005 | Smits et al. |
| 6,960,162 B2 | 11/2005 | Saadat et al. |
| 6,960,163 B2 | 11/2005 | Ewers et al. |
| 6,963,792 B1 | 11/2005 | Green |
| 6,974,411 B2 | 12/2005 | Belson |
| 6,976,991 B2 | 12/2005 | Hebert et al. |
| 6,984,203 B2 | 1/2006 | Tartaglia et al. |
| 7,029,435 B2 | 4/2006 | Nakao |
| 7,041,052 B2 | 5/2006 | Saadat et al. |
| 7,044,907 B2 | 5/2006 | Belson |
| 7,087,013 B2 | 8/2006 | Belson et al. |
| 7,090,637 B2 | 8/2006 | Danitz et al. |
| 7,090,683 B2 | 8/2006 | Brock et al. |
| 7,108,688 B2 | 9/2006 | Jensen |
| 7,128,708 B2 | 10/2006 | Saadat et al. |
| 7,169,141 B2 | 1/2007 | Brock et al. |
| 7,171,279 B2 | 1/2007 | Buckingham et al. |
| 7,182,731 B2 | 2/2007 | Nguyen et al. |
| 7,214,230 B2 | 5/2007 | Brock et al. |
| 7,232,434 B2 | 6/2007 | Suyama et al. |
| 7,250,027 B2 | 7/2007 | Barry |
| 7,322,935 B2 | 1/2008 | Palmer et al. |
| 7,338,505 B2 | 3/2008 | Belson |
| 7,398,781 B1 * | 7/2008 | Chin ............ A61B 17/00008 128/898 |
| 7,867,241 B2 | 1/2011 | Brock et al. |
| 8,298,161 B2 * | 10/2012 | Vargas .................. A61M 25/00 600/587 |
| 8,992,421 B2 | 3/2015 | Stand et al. |
| 9,591,964 B2 | 3/2017 | Choset et al. |
| 9,649,163 B2 | 5/2017 | Darisse et al. |
| 2002/0026096 A1 | 2/2002 | Motoki et al. |
| 2002/0062062 A1 | 5/2002 | Belson et al. |
| 2002/0161281 A1 | 10/2002 | Jaffe et al. |
| 2004/0073084 A1 | 4/2004 | Maeda et al. |
| 2005/0240078 A1 | 10/2005 | Kwon et al. |
| 2009/0171151 A1 | 7/2009 | Choset et al. |
| 2014/0005683 A1 | 1/2014 | Stand et al. |
| 2014/0318299 A1 | 10/2014 | Oyola et al. |
| 2014/0371764 A1 | 12/2014 | Oyola et al. |

FOREIGN PATENT DOCUMENTS

| WO | WO-2003092476 A2 | 11/2003 |
|---|---|---|
| WO | WO-2006083306 A2 | 8/2006 |

OTHER PUBLICATIONS

Brown et al., "Design and Control of a Second-Generation Hyper-Redundant Mechanism," International Conference of Robots and Systems, San Diego, CA, Oct. 29-Nov. 2, 2007.

Wolf et al., "A Mobile Hyper Redundant Mechanism for Search and Rescue Tasks," International Conference on Robots and Systems, Las Vegas, NV, Oct. 2003.

Borangiu T. et al., "Constrains-based Motion Planning for an Automatic, Flexible Laser Scanning Robotized Platform", 2008, IEEE, p. 1-5.

Ikuta K. et al., "Hyper Redundant Miniature Manipulator "Hyper Finger" for Remote Minimally Invasive Surgery in Deep Area",

(56) References Cited

OTHER PUBLICATIONS

2003, IEEE, International Conference on Robotics & Automation, Sep. 14-19, 2003, p. 1098-1102.
M. J. Mack., "Minimally Invasive and Robotic Surgery", JAMA, Feb. 7, 2001, vol. 285, No. 5, p. 568-572.

* cited by examiner

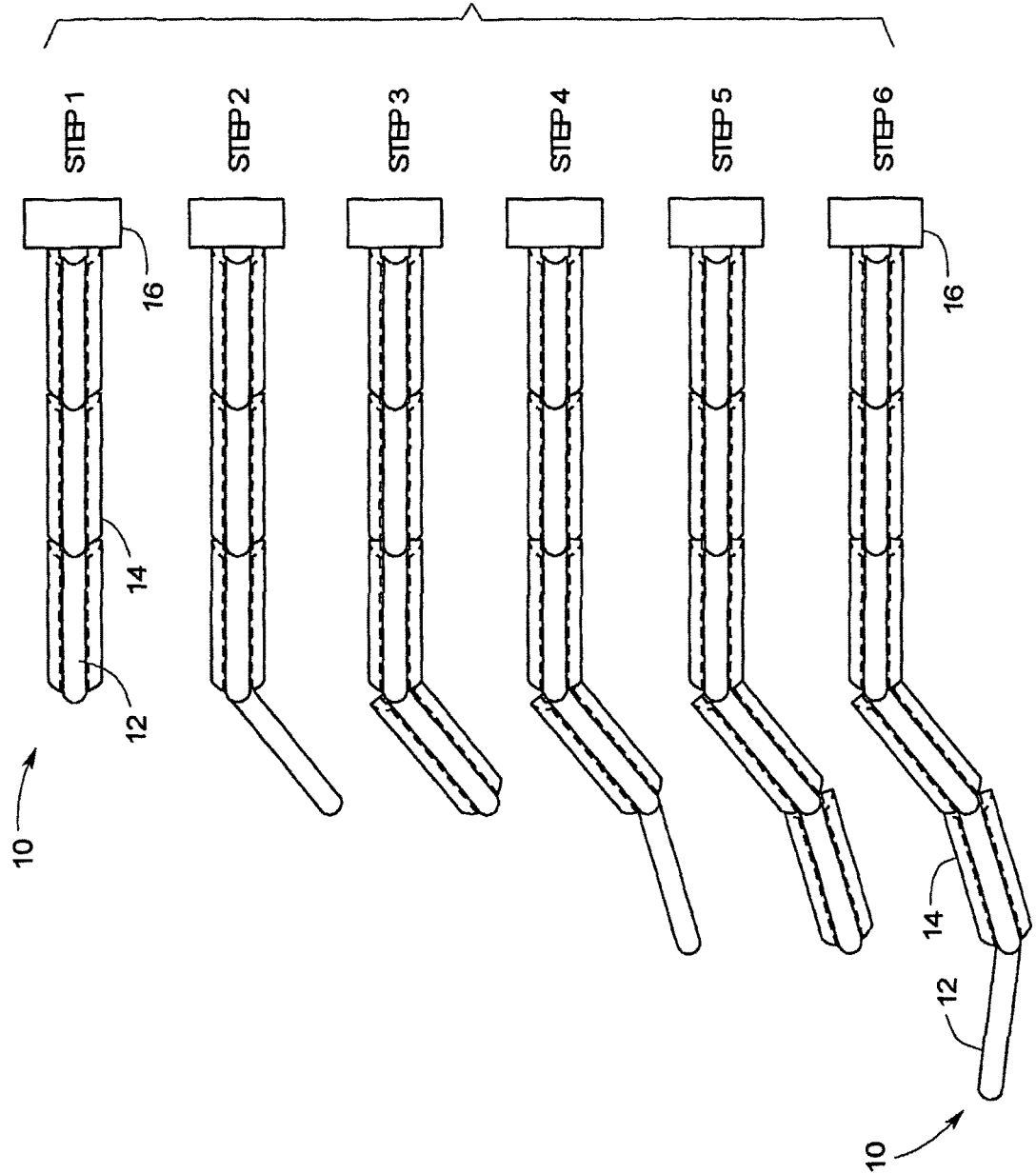

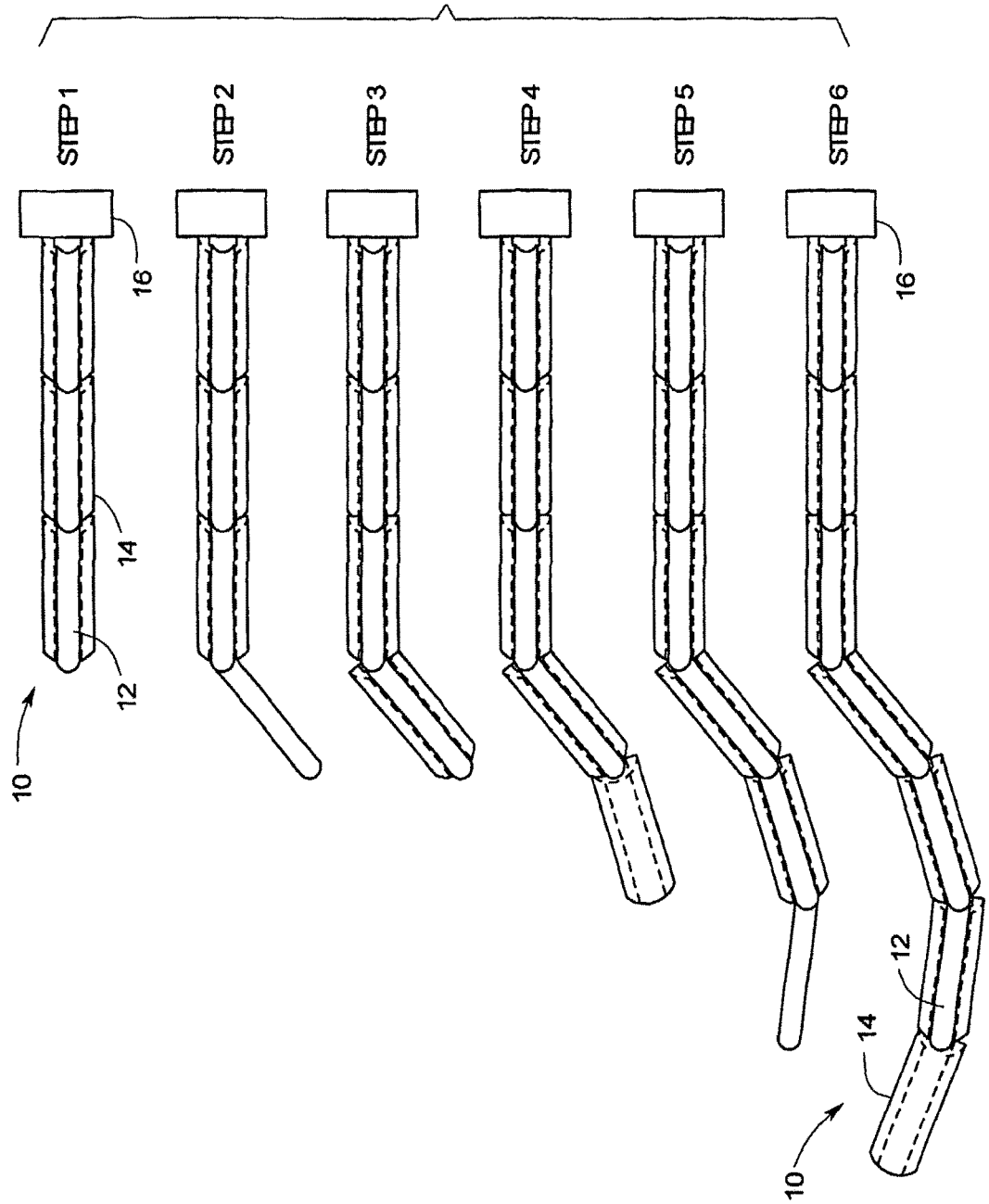

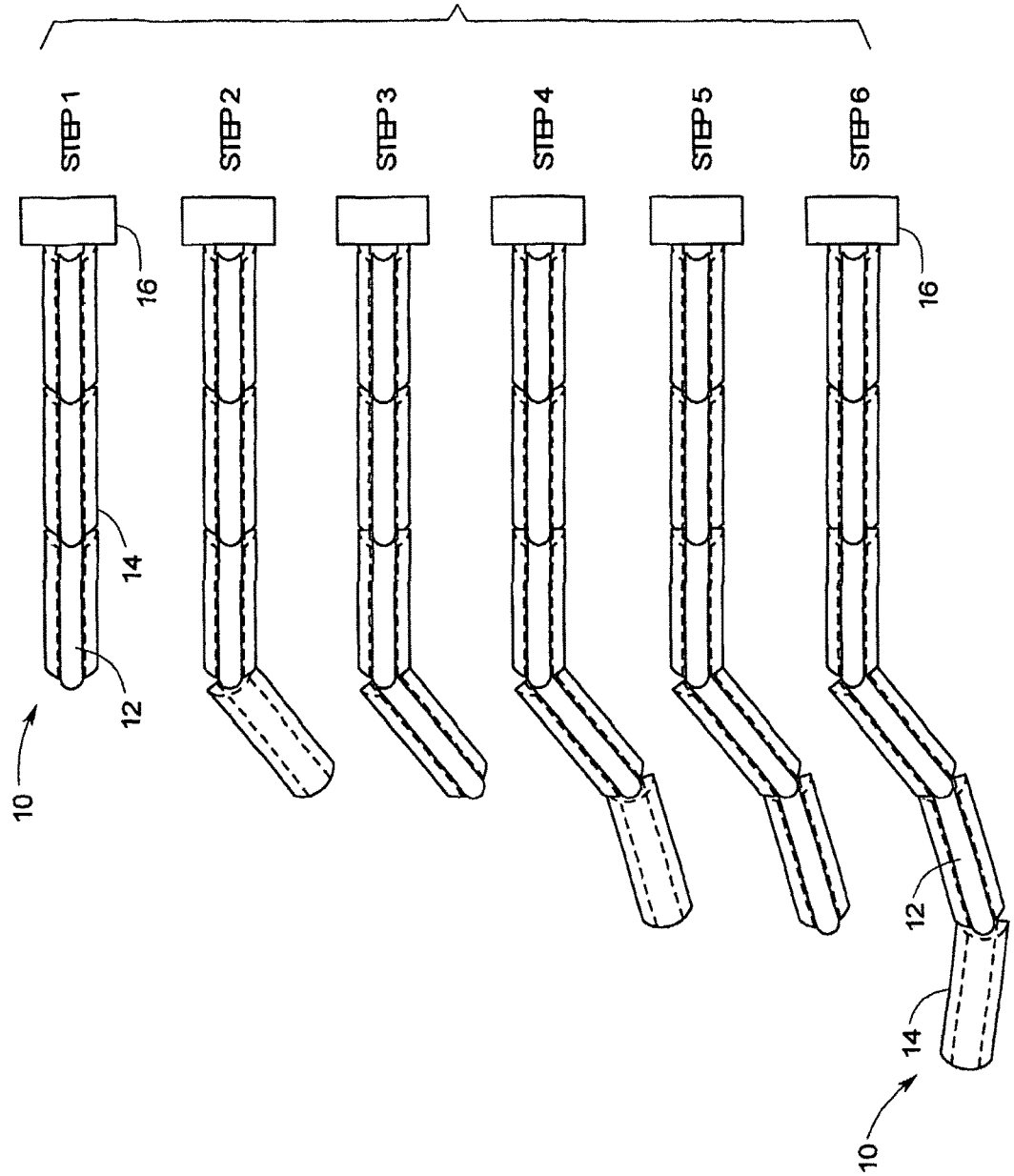

Bipolar H-Bridge

LINK i+ 1

LINK i

STEERABLE, FOLLOW THE LEADER DEVICE

This patent application claims priority to, and is a divisional of U.S. patent application Ser. No. 11/630,279, filed Dec. 20, 2006, entitled "Steerable, Follow the Leader Device", which is a national stage application of International Patent Application No. PCT/US2005/022442, filed Jun. 24, 2005, which claims the benefit of U.S. Application Ser. No. 60/583,094 entitled "Flexible Steerable Go-Anywhere Medical Snake Robot", filed Jun. 25, 2004, the disclosures of which are incorporated herein by reference in their entireties.

BACKGROUND

The present disclosure is an outgrowth from the field of robotics for the field of teleoperated mechanisms and, more particularly, to three dimensional, flexible, steerable devices.

Although there are many applications for this disclosed device, the motivating application for this device is minimally invasive surgery. There are few medical robotic systems available in the market today. These systems can be categorized into three major groups: active, semi-active, and passive robotic system. The active robotic system approach is represented by Kazanzides et al. [Kazanzides P, Mittelstadt B, Musits B, Barger W, Zuhars J, Williamson B, Cain P and Carbone E: An integrated system for cementless hip replacement. *IEEE Engineering in Medicine and Biology*. pp. 307-313, 1995] and Brandt et al. [Brandt G, Radermacher K, Lavalle S, Staudte H. W, Rau G, "A Compact Robot for Image Guided Orthopedic Surgery: Concept and Preliminary Results", *Lecture notes in Computer Science* 1205, *CVRMed-MRCAS'97*, Troccaz J, Grimson R, and Mosges R, eds, pp. 767-776, 1997] where, in the first example, a serial robot actively mills the femur to optimally fit an implant for a knee surgery. This robot is a serial-type mechanism with a large work volume relative to the task at hand. Therefore, such robots are somewhat cumbersome and heavy, and suffer several known drawbacks including relatively low stiffness and accuracy, and low nominal load/weight ratio. The fact that these robots are used for medical procedures, where accuracy and safety are paramount, has motivated researchers to look for manipulators with better kinematics and dynamic performance for specific surgical tasks.

In the second example, a Stewart platform is used in hip replacement surgery. A Stewart platform is a type of parallel robot. A six degree of freedom parallel robot is composed of two rigid platforms, one used as a base platform and the other as a moving end-effecter. The two platforms are connected by ball-and socket joints to six links capable of changing their length. By controlling the length of each link, the mechanism can position and orient the moving end-effecter relative to the base platform. Advantages of parallel robotic structures include: low weight, compact structure, high accuracy, high stiffness, restricted workspace, high frequency response, and low cost. [Merlet J.-P., Les Robots Paralleles, Hermes, Paris, 1997]. Moreover, parallel robots are significantly more robust to failure than serial devices because in a serial device, one failure can cause the robot to dramatically move, whereas in a parallel structure, one failure will have little effect on the overall motion of the robot. This is important in medical applications because surgeons want the device to maintain its last position in case of a catastrophic failure. [Khodabandehloo K., Brett P. N., Buckingham R. O., "Special-Purpose Actuators and Architectures for Surgery Robots", *Computer Integrated Surgery*, Taylor R., Lavalle S., Burdea G., Ralph Mosges, eds, pp. 263-274, 1996].

From a robotics perspective, the main drawback of parallel mechanisms is their limited workspace. However, as pointed out by Khodabandehloo et al., limited workspace is an advantage in medical applications because the active in-situ operation volumes are limited to protect the patient and physician. Unfortunately, this advantage forces the robot to be deployed near the operation site in the operating room, which is often unrealistic because the robot would interfere with the surgeons. One of the solutions introduced to solve this problem is to attach the entire robotic system to the operating room's ceiling so that the robot works "upside down." [Lueth T., Bier J., "Robot Assisted Intervention in Surgery", Gilsbach J. M. and Stiel H. S. (Editors), *Neuronavigation-Neurosurgical and Computer Scientific Aspects*, Springer-Verlag, Wien. 1999]. In this way, the robot does not interfere during the standard operating procedure, and is activated and maneuvered to the operating area when required. However, this solution is not applicable in all operating rooms and requires special operating room design.

The first known robot introduced to the operating room was the Robodoc™ system (Integrated Surgical Systems, Sacramento, Calif.). This robot is used to bore the medullary cavity of the femur for cementless femoral prostheses. Other robotic systems introduced in the market are the URS™, for positioning an endoscope in a tremor free and more precise way, i.e. with an accuracy of up to $\frac{1}{100}$ mm. EndoAssist™, used for camera support, EndoWrist™, used for instrument support, CASPAR™, used for hip replacement, AESOP™, used for camera support, and ZEUS™, for instrument support. Other available medical robotic systems are the Neuromate™, used for endoscope/catheter guidance, the MKM™, used for microscope support, and the SurgiScope™, also used for microscope support.

The semi-active robotic system approach is represented by Ho et al. [Ho S C, Hibberd R D, Davies B L, "Robot Assisted Knee Surgery", *IEEE Engineering in Medicine and Biology*, Vol. 14, pp. 292-299, May/June 1995], Kienzle et al. [Kienzle III, T, Stullberg D., Peshkin M., Quaid A., Lea J., Goswami A., Wu Ch., "A Computer-Assisted Total Knee Replacement Surgical System Using a Calibrated Robot", *In Computer integrated surgery*. Tatlor, Lavallee, Burdea, and Mosges, eds, MIT Press, pp. 410-416, 1996], and Harris et al. [Harris S J., Lin W J, Fan K L, Hibberd R D, Cobb J, Middelton R, Davies B L, "Experiences with Robotic Systems for Knee Surgery", *Lecture notes in computer science* 1205, *CVRMed-MRCASD* '97]. In Kienzle et al. the robot acts as an assistant during the operation by holding a tool in a steady position, accurately guiding a cutting tool, and preventing the tool from moving out of the desired operative region. A third approach, passive robotic systems, is represented by Grace et al. [Grace K. W., Colgate J. E., Gluksberg M. R., Chun J. H., "Six Degree of Freedom Micromanipulator for Ophthalmic Surgery", *IEEE International Conference on Robotics and Automation*, pp. 630-635, 1993], and Jensen et al. [Jensen P. S., Glucksberg M. R., Colgate J. E., Grace K. W., Attariwala R., "Robotic Micromanipulator for Orthopedic Surgery", *1st International Symposium on Medical Robotics and Computer Assisted Surgery*, pp. 204-210, Pittsburgh 22-24, 1994], where a six degree of freedom robot acts simply as a guided tool, fully controlled by the surgeon.

The third category of medical robots is the passive system. This kind of robotic system supports the surgical procedure, but takes no active part during surgery, in other words: the surgeon is in full control of the surgical procedure at all times. There are also few robotic systems which fall in this category. Matsen et. al. [Matsen FA III, Garbini J L, Sidles J A, Prat B, Baumgarten D, Kaiura R, Robotic assistance in Orthopedic surgery, Clin Orthp and Rela Res 296, 1993: 178-186.] report on a passive robotic system for knee arthroplasty. For their research they use a commercial Unimation PUMA 260, who hold a three dimensional transparent template which enables the surgeon to indicate the desired position of the prosthetic joint surface. The robot then places the saw guide such that the resulting cut plane agrees with the one indicated by the surgeon, who is actually the one holding the power saw and performing the cuts. This system was never used in the operating room.

McEwen et. al. [Mc Ewen C, Bussani C R, Auchinleck G F, Breault M J. Development and initial clinical evaluation of pre robotic and robotic retraction systems for surgery. 2$^{nd}$ Annual Int Symposium Custom Orthopaedic Prosthetics, Chicago, October 1989.] use Arthrobot as an assistant in the operating room. The robot is neumatically powered, electronically controlled positioner device which is used intraoperatively to hold the limb. The system has no sensing capabilities and is able to move only under explicit human control. The system was used during arthroplasties of the knee and hip.

Other passive robotic systems are reported by Grace et. al. [Grace K. W., Colgate J. E., Gluksberg M. R., Chun J. H. A Six Degree of Freedom Micromanipulator for Ophthalmic Surgery. IEEE International Conference on Robotics and Automation 1993; 630-635.] yet these are not related to orthopedic applications. Grace developed a six degrees of freedom micro manipulator which is used for treatment of retinal venous occlusion. During procedure, the operator is watching the robot's end-effector (using a microscop) and guiding it using a multi-dimensional joystick input device.

However, the most frequent examples of passive robotic systems are surgical navigation systems, as they represent the central element in each CAOS system [Nolte L P, Langlotz F, Basics of computer assisted orthopedic surgery (CAOS), Navigation and robotics in total joint and spine surgery, New York, Springer, 2004.] Basically, a navigation system refers the position i.e. location and orientation, of the acting components of the system to a global coordinate system, such that their relative position can be resolved in the global system.

The inventors of the current patent application have built many other types of robots. One of their specialties includes snake robots, formally called hyper redundant mechanisms. Snake robots can be used in an active, semi-active, and passive manner. The snake robot was designed and constructed originally to assist in search and rescue tasks. [Wolf, A, Brown, H. B., Casciola, R., Costa, A., Schwerin, M., Shamas, E., Choset, H., "A mobile hyper redundant mechanism for search and rescue tasks", *Proceedings of IEEE/RSJ IROS*2003]. The construction of this robot required a new mechanical design such that the robot would be stiff enough to support its own mass while consuming a minimum of power and volume. The new joints in this robot, designed and constructed in-house, have a large range of motion suitable for a hyper-redundant snake. [Shammas, E., Wolf, A., Brown, H. B., Choset, H., "New Joint Design for Three-dimensional Hyper Redundant Robots", *Proceedings of IEEE/RSJ IROS*2003]. The snake robot was attached on top of a mobile platform so that the snake could be semi-autonomously transported to the search area. Control of the mobile robot platform and the snake robot is performed through a joystick, to provide the user with a simple, intuitive interface. Snake robot control is performed within the reference frame of the camera, such that inputs from the joystick are converted into the camera reference frame. [Wolf, A, Choset, H., Brown, H. B., Casciola, R., "Design and Control of a Hyper-Redundant Mechanism", *Submitted to IEEE Transactions on Robotics*]. If this type of device can be built with a reduced cross-sectional diameter, then this type of snake robot can also be used to allow surgeons to reach areas of the body in a minimally invasive fashion and to perform operations with tools at the tip of the snake robot.

Virtually all previous work in hyper redundant robots focused on the mechanism development and end effecter placement. [Chirikjian G., S., Burdick W., J., (1995a) Kinematically optimal hyper-redundant manipulator configurations, *IEEE Tran. On Rob and Aut*, 11 (6), pp. 794-806] [Chirikjian G., S., Burdick W., J. (1995b) The kinematic of hyper-redundant robot locomotion, *IEEE Tran. On Rob and Aut*, 11(6), pp. 781-793] Most of these devices were limited to the large scale. Historically, Hirose, in 1972, developed an impressive device that mimicked the locomotion of real snakes on the ground [Hirose, S. Biologically Inspired Robots: Snake-like Locomotors and Manipulators. Oxford University Press: Oxford 1993]. Research continued in the early 1990's at Caltech with the planar hyper-redundant manipulator by Chirikjian and Burdick; their contribution focused on novel end effecter placement algorithms for these robots, not the robot itself (Chirikjian and Burdick, 1995). Recently, other researchers, such as Yim at Xerox Parc, Miller on his own and Haith at NASA Ames, have duplicated Hirose's pioneering work on snake locomotion, where Yim and Haith used Yim's polybot modules to form modular hyper-redundant mechanisms. Modularity clearly has its benefits, but comes at an unacceptable cost, which manifests itself in a loss of strength and maneuverability. The electromechanical connection is polybot's innovation, but it also provides a point of weakness to the mechanism and it occupies space that makes the robot more discrete (increase in link length, i.e., separation in degrees of freedom (DOF)) and hence reduces maneuverability. Modularity has more value when the target configuration of the robot is unknown a priori.

The challenge of a hyper redundant mechanism is to be strong enough to lift itself in three dimensions but be small and light enough to be useful to even demonstrate basic planning. The Pacific Northwest Labs developed a three-dimensional mechanism which was incredibly strong but moved too slowly and was too large. This robot moved too slowly because it was intended to be used for bomb disarming, so that a technician could tele-operate this robot to probe the internals of a bomb without accidentally detonating it. Kinematically, the mechanism is a sequence of linearly actuated universal joints stacked on top of each other. Takanashi developed at NEC a new two-DOF joint for snake robots that allowed a more compact design. This joint used a passive universal joint to prevent adjacent bays from twisting while at the same time allowing two degrees of freedom: bending and orienting. This universal joint enveloped an angular swivel joint, which provided the two degrees of freedom. The universal joint being installed on the outside rendered the joint too bulky. Researchers at Jet Propulsion Laboratory (JPL) "inverted" Takanashi's design by placing a small universal joint in the interior of the robot. This allowed for a more compact design, but came at the cost of strength and stiffness (backlash). A small universal joint cannot transmit rotational motion at big deflection angles nor can it withstand heavy loads.

For certain applications it is desired that the hyper redundant robot operate on the size of less than 15 mm diameter that is normally required for minimally invasive surgery. The many degrees of articulation that furnish the hyper redundant robot with its enhanced capabilities also offer its main research challenges. There are several critical challenges that one must address to build a hyper redundant robot. First, there is the actual mechanical design itself; constructing a device that has high maneuverability in a small confined volume. Low level control is another challenge in such small scales. The compact space inside the device envelop leaves little room for wiring all actuators and sensors on board the hyper redundant robot, hence a more advanced low level controller should be used.

One avenue of research to reduce the size of hyper redundant robots has focused on exotic actuator development such as shape memory alloys. Numerous works have been presented on active catheters and endoscopes, most actuated by shape memory alloys (SMA) actuators (Tohuko University, Olympus Optical Co). SMA spring and wire actuation has been implemented by Hirose [Hirose, S. Biologically Inspired Robots: Snake-like Locomotors and Manipulators. Oxford University Press: Oxford 1993] to overcome hysteresis problem of the SMA material. The Santa Anna laboratory in Pisa Italy (Dario et. al 2000), developed an arthroscope tool which is cable actuated; a position sensor detects the tip location and a force sensor detects contact forces. Overall accuracy of the device is 2.3 mm. Other endoscope like active mechanisms are the Laboratorie de Robotque de Paris (LRP), 8 mm in diameter worm like mechanism which is formed by a sequence of segments articulated to each other by SMA actuated pin joints [Kuhl C., Dumont G., Virtual endoscopy: from simulation to optimization of an active endoscope. Proc. Of the modeling & simulation for computer aided medicine and surgery 2002, 12, pp 84-93]. The device is specifically designed to explore the intestine with a camera. An electrostrictive polymer artificial muscle (EPAM) based snake like endoscopic robot was developed at Stanford Research Institute (SRI). That device is composed of several blocks joined by a concentric spine [Kornbluh R D., Pelrine R., Eckerle J., Joseph J., Electrostrictive polymer artificial muscle actuators. Proc. Of the IEEE in Conf. on Robotics and Automation 1998, pp 2147-2154]. Researchers at Pennsylvania state university [Frecker M I., Aguilera W M., Analytical modeling of a segmented unimorph actuator using electroactive (pvdf-trfe) copolymer. Smart material and structures 2003, pp 82-91] have also developed a snake like manipulator using electrostrictive polymer artificial muscle. Their special design of the actuator allows control of the curvature.

As an alternative to an articulated probe, researchers have considered a mobile type of robot that resembles a miniature inch worm for both pipe inspection and medical procedures. Several manuscripts have been published regarding miniature inchworm-like mechanisms which are capable of maneuvering within rigid pipes. The Kato device [Kato S., Hirayama T., Fabrication of a high speed in-pipe mobile micro machine. Proc. of the 4$^{th}$ Japan-France Congress and 2$^{nd}$ Japan-Europe congress on Mechatronics, 1998, 1, pp 429-432] is a 96 mm long, 18 mm in diameter mechanism which is capable of moving inside tubes using stick and slip strategy. This mechanism is not designed to move itself within a deformable environment (intestine). The walking work by Sanata Anna University is a 90 mm long, 18 mm in diameter SMA based worm like manipulator which clamps itself into the environment and then manipulates itself forward [Dario P., Menciassi A., Park J H., Lee L., Gorinil S., Park J., Robotic solutions and mechanisms for a semi-automated endoscope. Proc. of the IEEE/RSJ international conf. on robotic systems, 2002, p. 1379-1384.

Focusing now on basic research specific to medical articulated probes, in Geunbae L., Kazuyuki M., Keisuke Y., Masahisa S., et. al (1996) Multi-link active catheter snake-like robot, *Robotica,* 14, pp. 499-506, the researchers developed a 2.8 mm diameter active catheter based on silicon micromachining. This multilane manipulator is connected by joints made of shape memory actuators (SMA), fixed at equilateral triangular locations to allow bending in several directions. In this design an indirect heating was developed due to the SMA when the control system was integrated into the manipulator. Other endoscopic, SMA based, tools are presented in [Nakamura Y., Matsui A., Saito T., Yoshimoto K., (1995) Shape-memory-alloys active forceps for laparoscopic surgery, *IEEE int. Cof. on Robotics ad Automation*, pp. 2320-2327]; [Ikuta K., Tsukamoto M., Hirose S., (1988) Shape memory alloys servo actuator system with electric resistance feedback and application for active endoscope, *Proc. Of IEEE In Conf. Rob. And Aut.* pp. 427-430]; [Ikuta K, Nolata M., Aritomi S., (1994a) Hyper redundant active endoscope for minimally invasive surgery, *Proc. Of the first symposium on medical robotics and computer assisted surgery*, Pittsburgh, Pa., pp. 230-237]; [Ikuta K., Nokata M., Aritomi S., (1994b) Biomedical micro robot driven by miniature cybernetic actuator, *IEEE Int. Workshop on MEMS*, pp. 263-268]; [Dario P., Carrozza M. C., Lencioni L., Magnani B., et. al, (1997a) A micro robotic system for colonoscopy, *Proc. Int. Conf. Rob. and Aut.* pp. 1567-1572]; [Reynaerts D., Peirs J., Van Brussel H., (1999) Shape memory micro-actuation for a gastro intestinal intervention system. *Sensor and actuators,* 77, pp. 157-166]. However, those tools have relatively low stiffness, and they require high activation voltage. Hence, heat removal becomes a challenge. A different activation concept is presented in [Piers J., Reynaerts H., Van Brussel H., De Gersem G., (2003) Design of and advanced tool guiding system for robotic surgery, *IEEE Int. Conf. Rob and Aut,* pp. 2651-2656]. In that work, the authors presented a 5 mm diameter wire driven two degrees of freedom snake robot tool using super-elastic NiTi [Simaan N., Taylor R., and Flint P., (2004) A Dextrous System for Laryngeal Surgery: Multi-Backbone Bending Snake-Like Robot for Dexterous Surgical Tool Manipulation. IEEE Transaction of ICRA 2004, New Orleans]. Other devices are reported in Reynaerts D., Peiers L., Van Brussel H., Design of a shape memory actuated gastrointestine intervention system. Proc. of the int. Cof of new actuation 1997, Epacenet mechanism and Young ML., Jinhee L., Jisang P., Byugkyu K., Jong Oh P., Soo Hyun K., Yeh-Sun H., Self propelling endoscopic system. Proc. of the 2001 IEEE/RSJ Int. Conf. on intelligent robotic systems. 2002, pp 117-1122. However, wire actuation, SMA, and EPAM actuation become challenges with robots having multiple degrees of freedom due to minimal space inside the robot's mechanical envelope. Therefore, most of these systems were developed to be introduced into a confined tube-like environment or work as bending mechanisms not capable of generating a 3D curve (e.g. double non-planar "S" shape).

Robert Sturges' U.S. Pat. No. 5,759,151, which is hereby incorporated by reference in its entirety, discloses a flexible, steerable device for conducting exploratory procedures. The device includes at least one spine, each having stiffening means for selectively rendering the spine rigid and flexible along its length. A flexible sheath surrounds the spine and is axially slidably moveable relative to the spine so that the sheath will follow and conform to the shape of a spine in the rigid state and resist further flexure when the spine is in a relaxed state. A steerable distal tip is provided on the distal end of the device. Controls for the distal tip are mounted on the proximal end of the device. Mechanisms are provided on the distal end of the device for selectively activating and deactivating the stiffening means of the spine. An instrument conduit may be mounted on the sheath.

U.S. Pat. No. 6,610,007 discloses a steerable endoscope having an elongated body with a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion. Another desired path is selected with the selectively steerable distal portion and the endoscope body is advanced again. As the endoscope body is further advanced, the selected curves propagate proximally along the endoscope body, and when the endoscope body is withdrawn proximally, the selected curves propagate distally along the endoscope body. This creates a serpentine motion in the endoscope body allowing it to negotiate tortuous curves along a desired path through or around and between organs within the body.

SUMMARY OF THE PRESENT DISCLOSURE

A steerable, follow the leader device is disclosed which is capable of steering anywhere in three dimensions, such as, but not limited to, cluttered intracavity spaces, as well as the inside of a natural pathway such as a pipe, tube, intestines, or blood vessels, to name a few. The device is comprised of a first mechanism having a plurality of links and a first locking device for enabling the first mechanism to have a rigid state and a limp state. A second mechanism is comprised of a plurality of links and a second locking device enabling the second mechanism to have a rigid state and a limp state, and wherein at least one of the first and second mechanisms, or both, are steerable. In this embodiment, the first and second mechanisms may be positioned side by side or one within the other.

Another embodiment of the present disclosure is directed to a highly articulated probe comprising an inner core having a plurality of links and an outer sleeve having a plurality of links. A first wire extends through either the plurality of links of the inner core or the plurality of links of the outer sleeve and a plurality of wires runs through the other of the plurality of links of the inner core or the plurality of links of the outer sleeve. A device produces command signals. An electromechanical feeder is responsive to the command signals for alternating each of the inner core and the outer sleeve between a limp mode and a rigid mode and for advancing and retracting the inner core and the outer sleeve. In this embodiment, at least one of the inner core or the outer sleeve, or both, are steerable.

According to an embodiment of the present disclosure, a method of operating a follow the leader type of device is comprised of controlling the states of a first mechanism and a second mechanism such that one mechanism is rigid and one mechanism is limp, advancing the limp mechanism a predetermined distance, changing the states of the mechanisms, and repeating the advancing and changing until the device is positioned as desired. In this method, steering may be accomplished by steering the first mechanism while it is limp, or steering the second mechanism while it is limp, or by steering both mechanisms when they are limp.

According to another embodiment of the present disclosure, a method of moving a steerable, follow the leader device in a three dimensional space is comprised of generating images from a device mounted on the end of the steerable, follow the leader device. The steerable follow the leader device can be constructed according to any of the embodiments discussed above. The images are used to control the movement of the follow the leader device. The device mounted on the end of the follow the leader device includes one of a camera or a lens and light pipe. The method can be carried out in real time. When the space is the pericardium, the method additionally comprises making an incision below the xiphoid process and inserting the steerable, follow the leader device into the incision.

BRIEF DESCRIPTION OF THE DRAWINGS

For the present disclosure to be easily understood and readily practiced, various embodiments of the present disclosure will now be described, for purposes of illustration and not limitation, in conjunction with the following figures wherein:

FIGS. 1A-1C are graphic demonstrations of the concept of the present disclosure;

DESCRIPTION

Figure 2A:
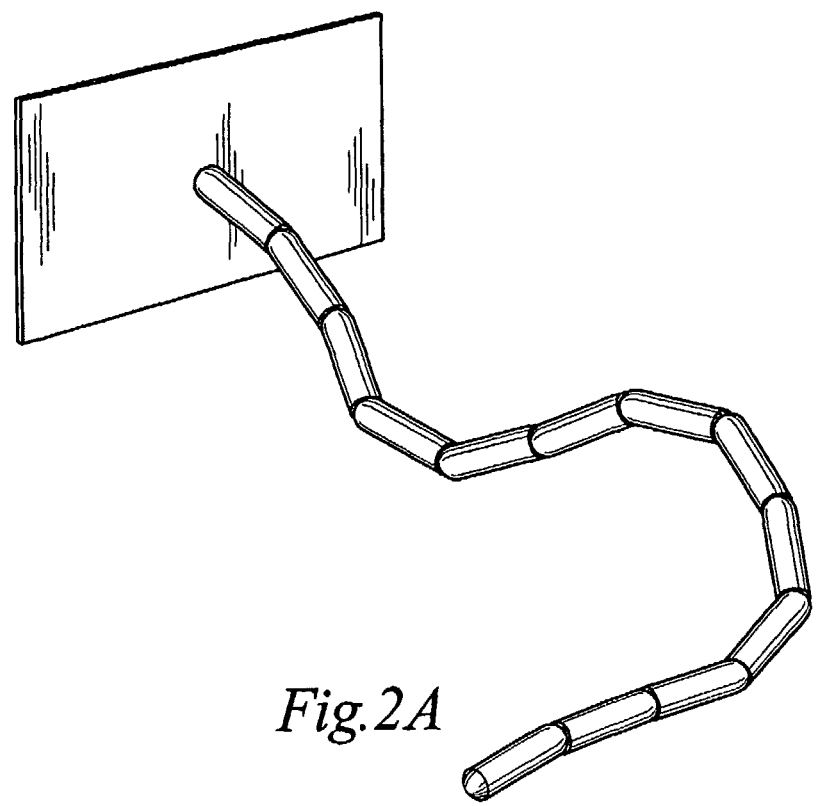
FIGS. 2A-2D illustrate various configurations assumed by a prototype of one embodiment of the disclosed device.
Figure 2B:
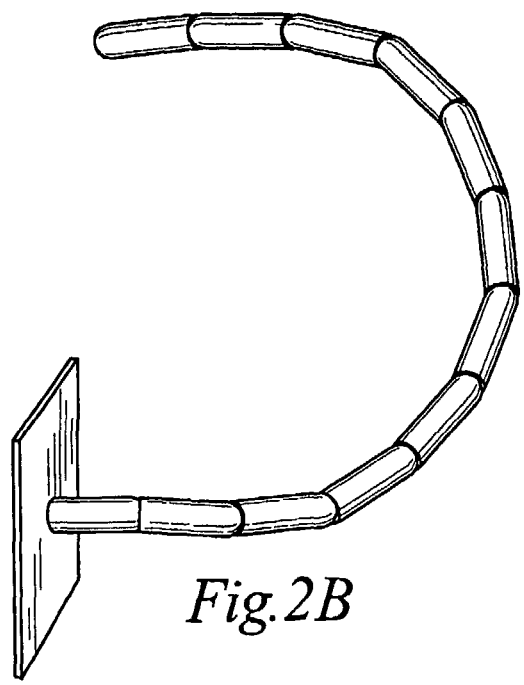
Figure 2C:
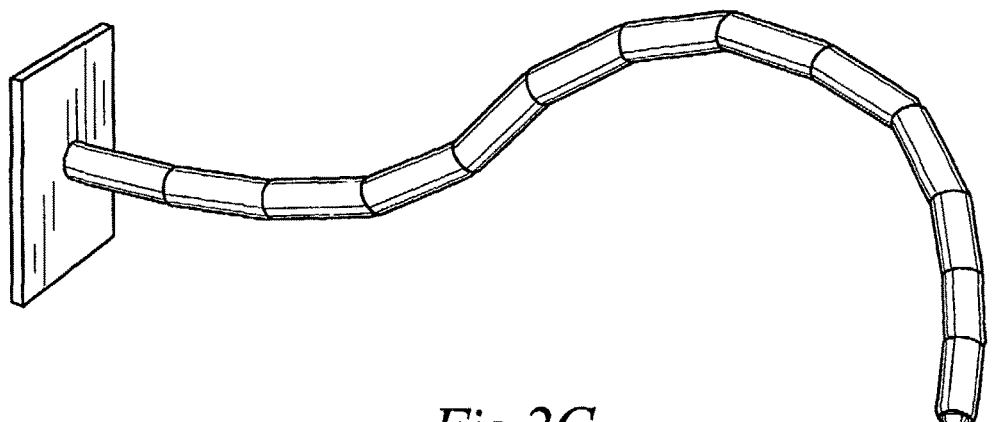
Figure 2D:
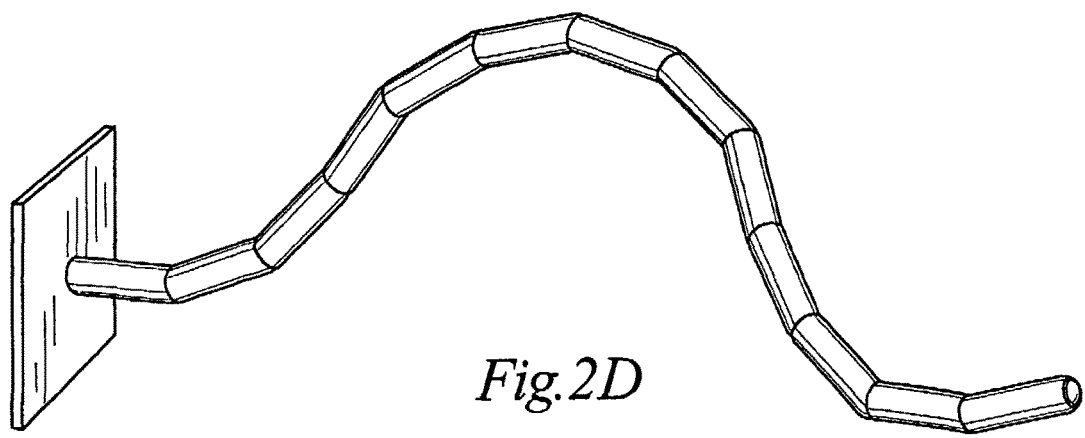
Figure 3A:
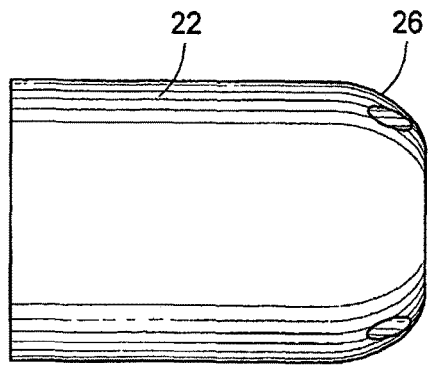
FIGS. 3A-3D illustrate various views of a cylinder of the outer sleeve.
Figure 3B:
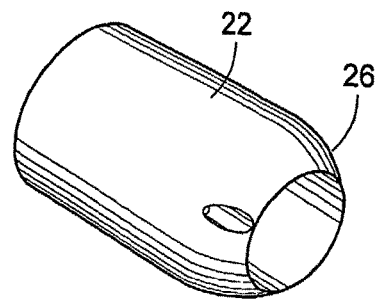
Figure 3C:
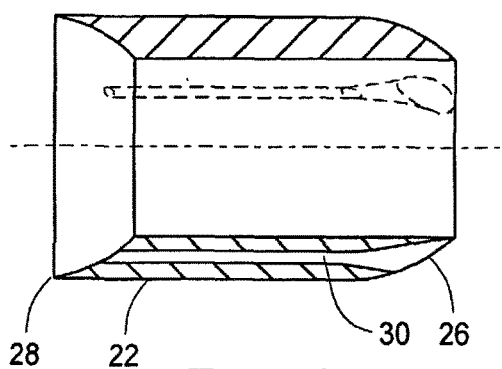
Figure 3D:
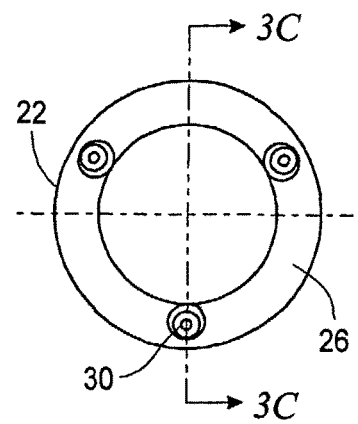
Figure 4B:
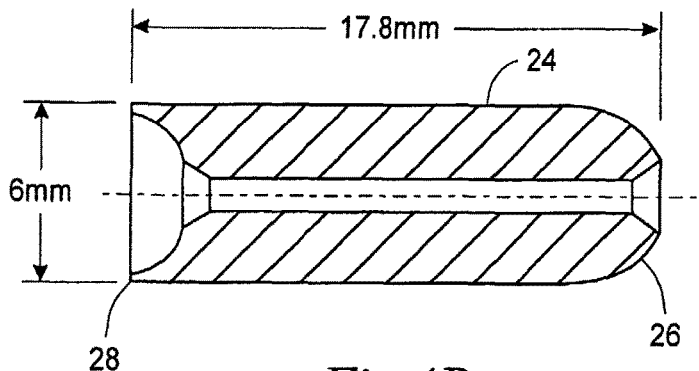
FIGS. 4A and 4B illustrate end and cross-sectional views, respectively, of a cylinder of the inner core.
Figure 4A:
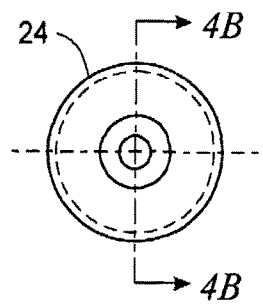

A highly articulated robotic probe (HARP) 10 of one embodiment of the present disclosure shown in FIGS. 1A-1C is essentially two concentric mechanisms, an outer one and an inner one, each of which can be viewed as a steerable mechanism. FIGS. 1A-1C show the concept of how different embodiments of the HARP 10 operate. Referring to FIG. 1A, we call the inner mechanism a first mechanism or inner core mechanism 12. We call the outer mechanism a second mechanism or sleeve mechanism 14. Each mechanism can alternate between being rigid and limp. In the rigid mode or state, the mechanism is just that—rigid. In the limp mode or state, the mechanism is highly flexible and thus either assumes the shape of its surroundings or can be reshaped. It should be noted that the term "limp" as used herein does not denote a structure that passively assumes a particular configuration dependent upon gravity and the shape of its environment; rather, the "limp" structures described in this application are capable of assuming positions and configurations that are desired by the operator of the device, and therefore are articulated and controlled rather than flaccid and passive.

With this HARP 10, one mechanism starts limp and the other starts rigid. For the sake of explanation, assume the sleeve 14 is rigid and the core 12 is limp, as seen in step 1 in FIG. 1A. Now, the core 12 is both pushed forward by a feeding mechanism 16, described below, and its "head" or distal end is steered, as seen in step 2 in FIG. 1A. Now, the core 12 is made rigid and the sleeve 14 is made limp. The sleeve 14 is then pushed forward until it catches up or is coextensive with the core 12, as seen in step 3 in FIG. 1A. Now, the sleeve 14 is made rigid, the core 12 limp, and the procedure then procedure repeats. One variation of this approach is to have the sleeve 14 be steerable as well. The operation of such a device is illustrated in FIG. 1B. In FIG. 1B it is seen that each mechanism is capable of catching up to the other and then advancing one link beyond. That requires an additional camera on the sleeve 14 but would potentially allow for quicker deployment of the HARP 10. In the current rendition, the sleeve 14 is steerable and the core 12 is not. The operation of such a device is shown in FIG. 1C.

In medical applications, once the HARP 10 arrives at a desired location, the surgeon can remove the inner core 12 and slide either a conventional device or a custom tool through the rigid sleeve 14 to perform various operations.

The HARP 10 is not limited to surgery, but can be used in engine inspection, engine repairs, and engine retrofitting. Other applications include tank inspection, spying or surveillance applications, bomb disarming, and inspection or repairs in tightly confined spaces such as submarines or within nuclear weapons. Other applications include structural (e.g. building) inspections, hazardous waste remediation and bioterrorists sample recovery. Clearly, the device of the present disclosure has a wide variety of applications and should not be taken as being limited to any particular application.

The HARP 10 of the present disclosure device bears some similarities to Bob Sturges' patented device (U.S. Pat. No. 5,759,151) although the present disclosure incorporates several major innovations. First, the core 12 and/or sleeve 14 is steerable. Second, the sleeve 14 can be made both rigid and limp. These two innovations allow the HARP 10 to drive anywhere in three-dimensions. Sturges' device assumes that it is moving through a tubular space, such as the large intestines. Sturges' device requires that the intestines shape the device as it goes. As Sturges' device propagates out it, cannot "remember" its previous configuration and hence cannot keep the path it followed due to the fact that it is composed of only one element that can become both rigid and stiff. The HARP 10 can "remember" its previous configurations and for this reason, the HARP 10 can go anywhere in a three dimensional volume such as the intracavity spaces in a body. FIGS. 2A-2D illustrate various configurations assumed by a prototype of the device 10.

Figure 17:
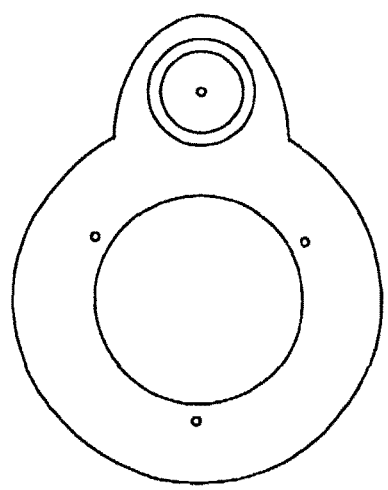
FIG. 17 illustrates another embodiment of a link which may be used in the device of the present disclosure.

The following discussion contains details of a preferred embodiment. The reader should recognize that the present disclosure is not to be limited by the detailed information that follows. Rather, the detailed information is intended for purposes of illustration and not limitation. As can be seen in FIGS. 3A-3D and 4A and 4B the sleeve 14 and core 12, respectively, are made up in this embodiment of concentric cylinders 22, 24, respectively, although links of other shapes may be used, e.g. a dogbone configuration (not shown) as well as links of a type that are not concentric, e.g. backbone configuration (see FIG. 17), among others. The ends of the cylinders 22, 24 are not flat but instead one end 26 is an "outer" or convex hemisphere and the other end 28 is an "inner" or concave hemisphere, both with the same radius of curvature R. The cylinders 22, or links, of the outer sleeve 14 are "chained" back-to-back such that the concave end 28 of one mates with the convex end 26 of an adjacent cylinder. Similarly, the cylinders 24, or links, of the inner core 12 are chained back-to-back. The result is a spherical-like joint, from a kinematic point of view. In the current embodiment, each link is able to rotate on the adjacent link's head, acting as a spherical joint with approximately 14° range of motion in any direction, although other ranges of motion are possible. The cylinders 22 have three channels 30 extending therethrough for control wires.

Figure 5A:
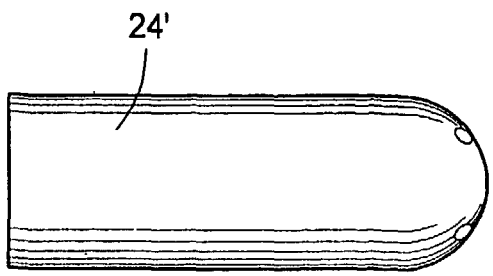
FIGS. 5A-5D illustrate various views of another embodiment of a cylinder of a steerable inner core.
Figure 5B:
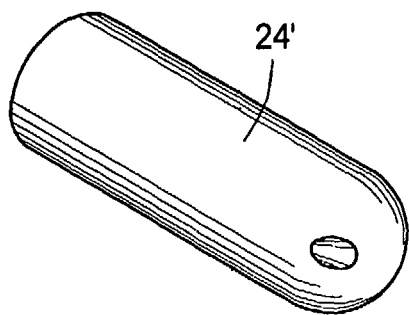
Figure 5C:
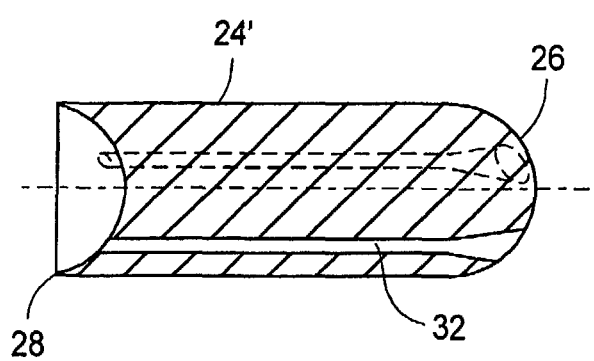
Figure 5D:
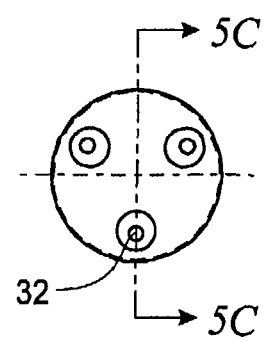

FIGS. 5A and 5B illustrate another embodiment in which the core 14 is steerable. The core 14 of this embodiment is comprised of cylinders 24' which have a convex 26 and concave 28 end. However, the cylinders 24' have three channels 32 for control wires.

The heads (i.e. the distal cylinders) of both the sleeve 14 and the core 12 are steerable using three cables which are attached at, for example, 120° from each other. As can be seen in FIGS. 3A-3D and FIGS. 5A-5D, there are three small cylindrical channels 30, 32, respectively, for wires to pass through. In the version of the device shown in FIGS. 4A and 4B, the inner cylinder 24 has only one wire, in which case there is only one hole 34 through its center.

It will be appreciated that although the preferred embodiment described above utilizes cables or wires, alternative means of manipulating the limp elements, such as miniature pneumatic or hydraulic cylinders or other mechanical linkages situated between individual links, can be employed without falling outside the scope of this invention.

The links, and hence the HARP 10, can be made out of virtually any material, including plastic, which allows it to be used online with NMR. One current prototype of our device has an outer diameter of the outer sleeve 14 of 12 mm and an outer diameter of the inner core 12 of 6 mm. The choice of 12 mm is based on available port sizes. Each link of the outer sleeve 14 weighs 1.5 grams and each link of the inner core 12 weighs 0.5 grams. Currently, the number of links in each of the inner core 12 and outer sleeve 14 is seventeen. Therefore, the total weight of the device 10 is thirty-four grams and its total length is 300 mm. These dimensions are intended for purposes of illustration and not limitation.

As noted, the core 12 and sleeve 14 can be made rigid or limp using wires or cables. Although there are many variations, in the current prototype the outer sleeve 14 consists of a set of cylinders 22 strung on three wires. The three wires are 120° apart, making it possible to steer in any direction. This design provides a radius of curvature of approximately eight centimeters. When the wires are pulled towards the back of the sleeve 14, the cylinders 22 are pulled towards each other. When the pulling force increases, the friction force between adjacent cylinders 22 increases until the whole outer sleeve 14 stiffens (i.e. enters the rigid mode). When the pulling force is released, the outer sleeve 14 becomes limp. Thus, the wires together with their respective motors form a locking device. The motors, along with the electronics for controlling the motors, form a means for controlling the tension on the wire. When the outer sleeve 14 is positioned one cylinder in front of the inner core 12, and the inner core 12 is stiff, the distal link of the outer sleeve 14 can be oriented by pulling one or more of the three wires. The magnitude of the pulling force which is exerted on each wire can be controlled. By pulling the three wires with the same magnitude, the outer sleeve 14 becomes stiff without changing its shape.

The inner core 12, like the outer sleeve 14, consists of a set of cylinders. In contrast to the outer sleeve 14, the inner core 12 does not need (but may optionally have) a steering ability. The inner core 12 does need the ability to change from rigid mode, to limp mode, and back. Therefore, in embodiments where the inner core 12 need not be steerable, the links of the inner core 12 may be strung on a single wire, which enables a small diameter for the device 10.

Figure 6A:
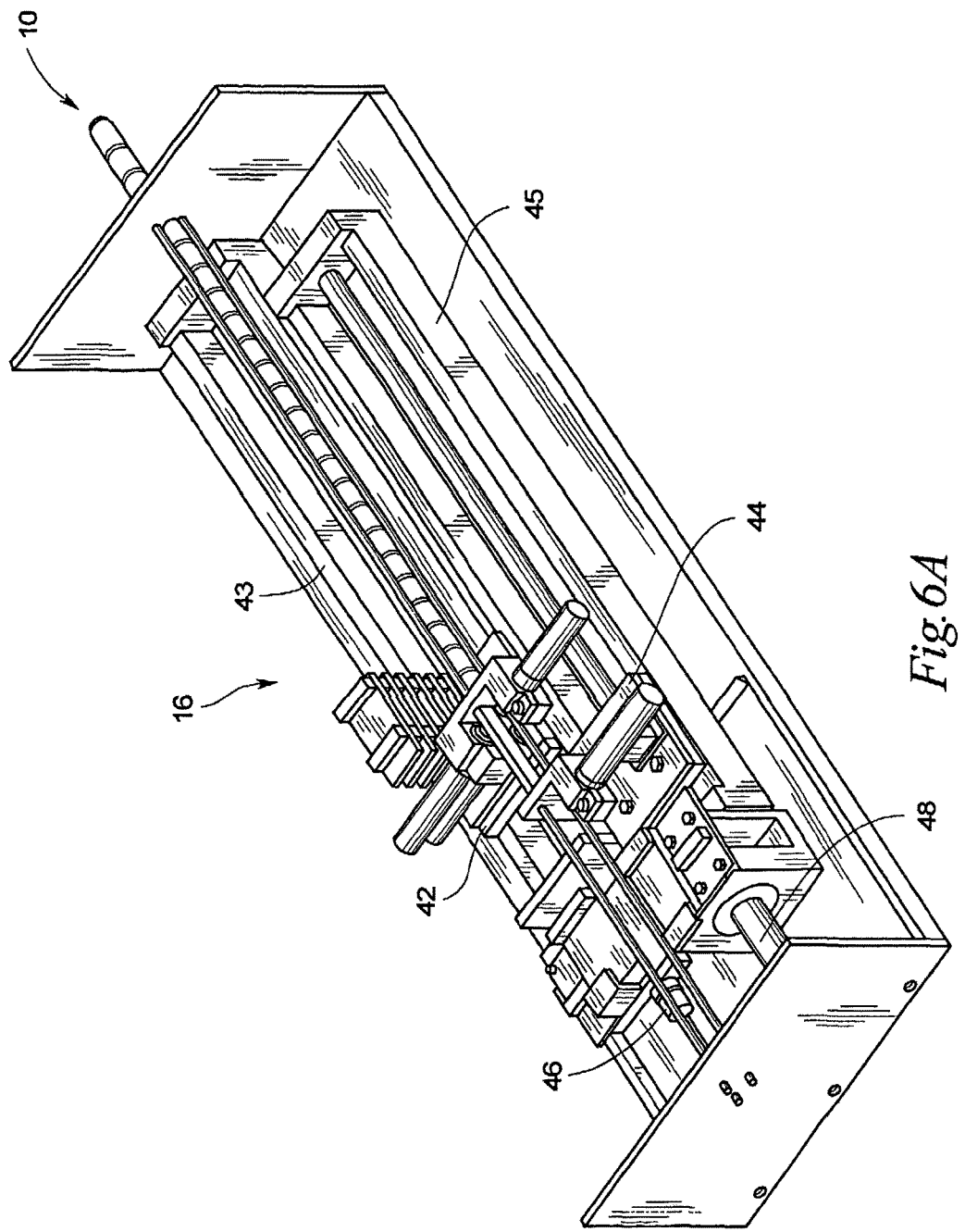
FIGS. 6A and 6B illustrates one example of a feeder mechanism.
Figure 6B:
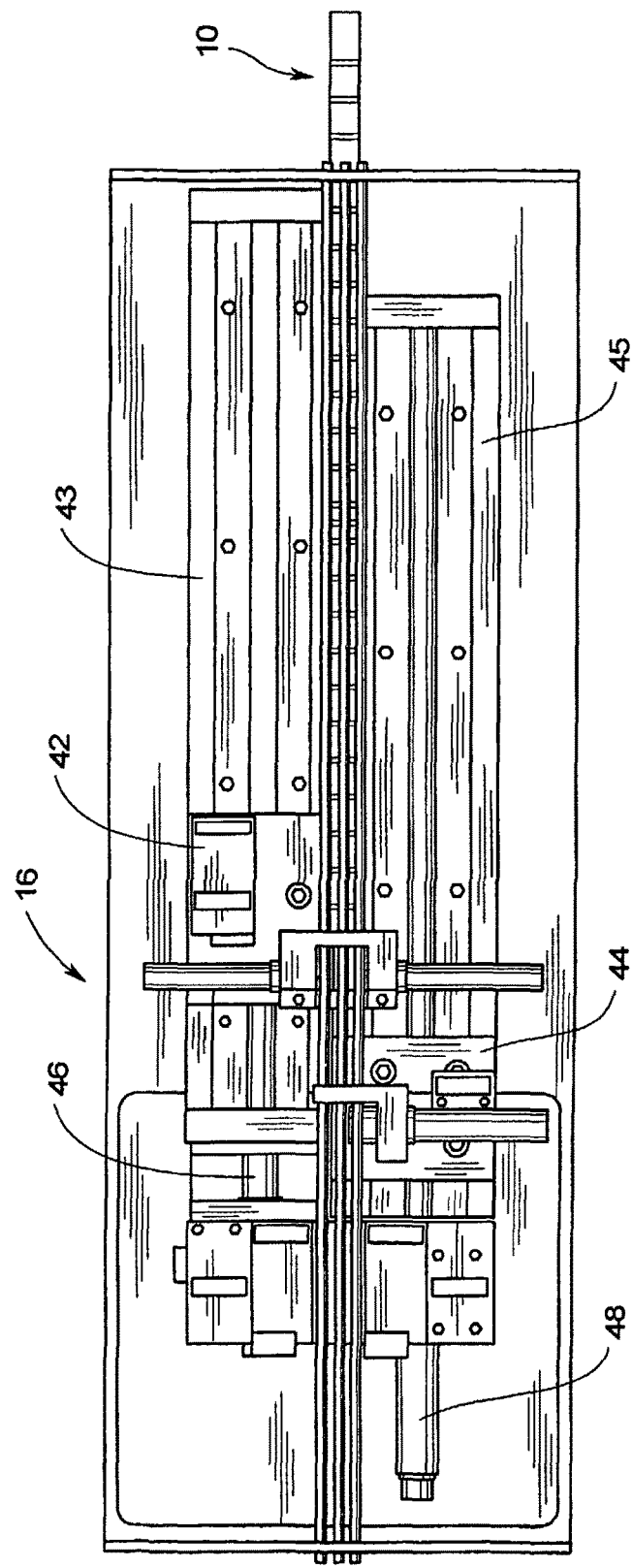

One type of feeding mechanism 16, shown in FIGS. 6A and 6B, inserts and retracts the HARP 10 into and out of, respectively, a region of interest. The feeder 16 has two movable carts. A first cart 42, carried in a first fixed tray 43, drives the outer sleeve 14 while a second cart 44 carried in a second fixed tray 45 drives the inner core 12. Each cart 42, 44, and hence each of the inner core 12 and outer sleeve 14, is driven independently by separate linear actuators 46, 48 respectively. The linear actuators 46, 48 may carry shaft encoders (not shown) used for position control as is known.

Figure 7:
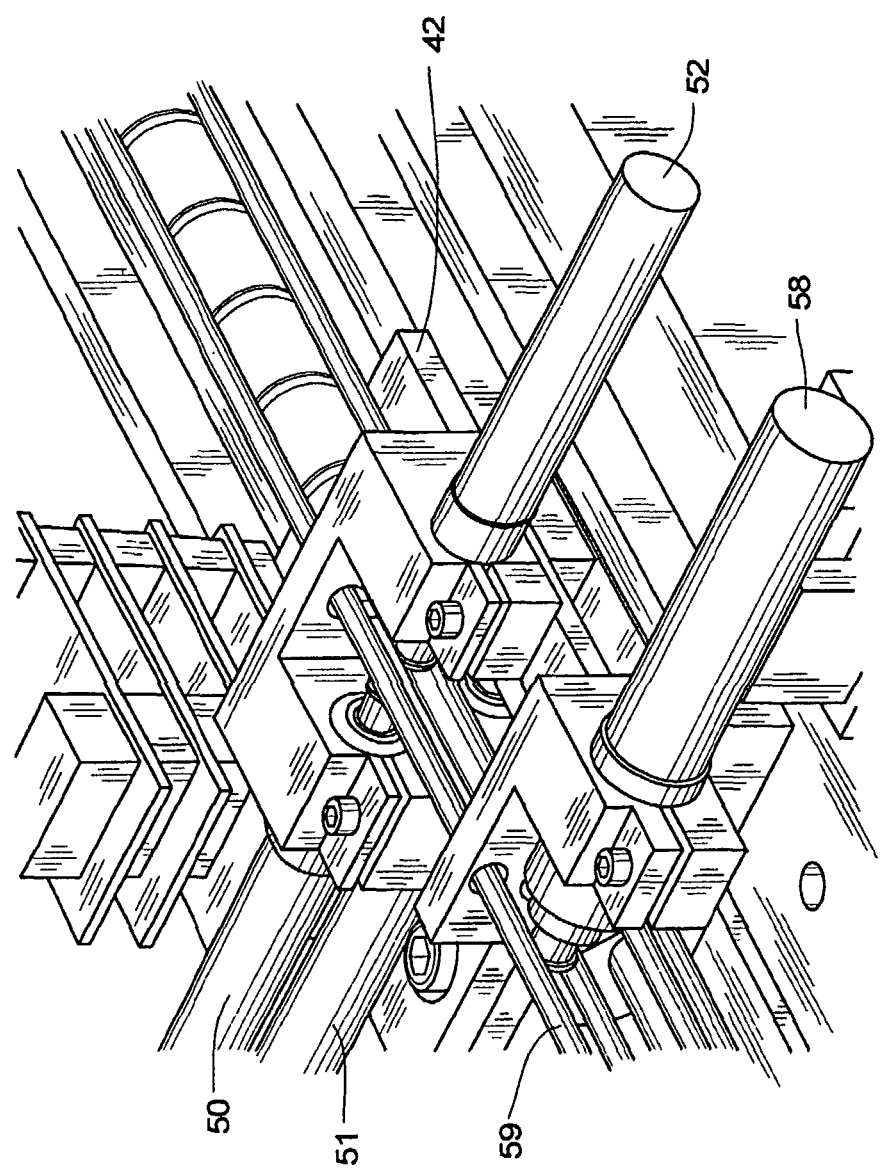
FIG. 7 illustrates devices for controlling the tension on the wires.
Figure 8:
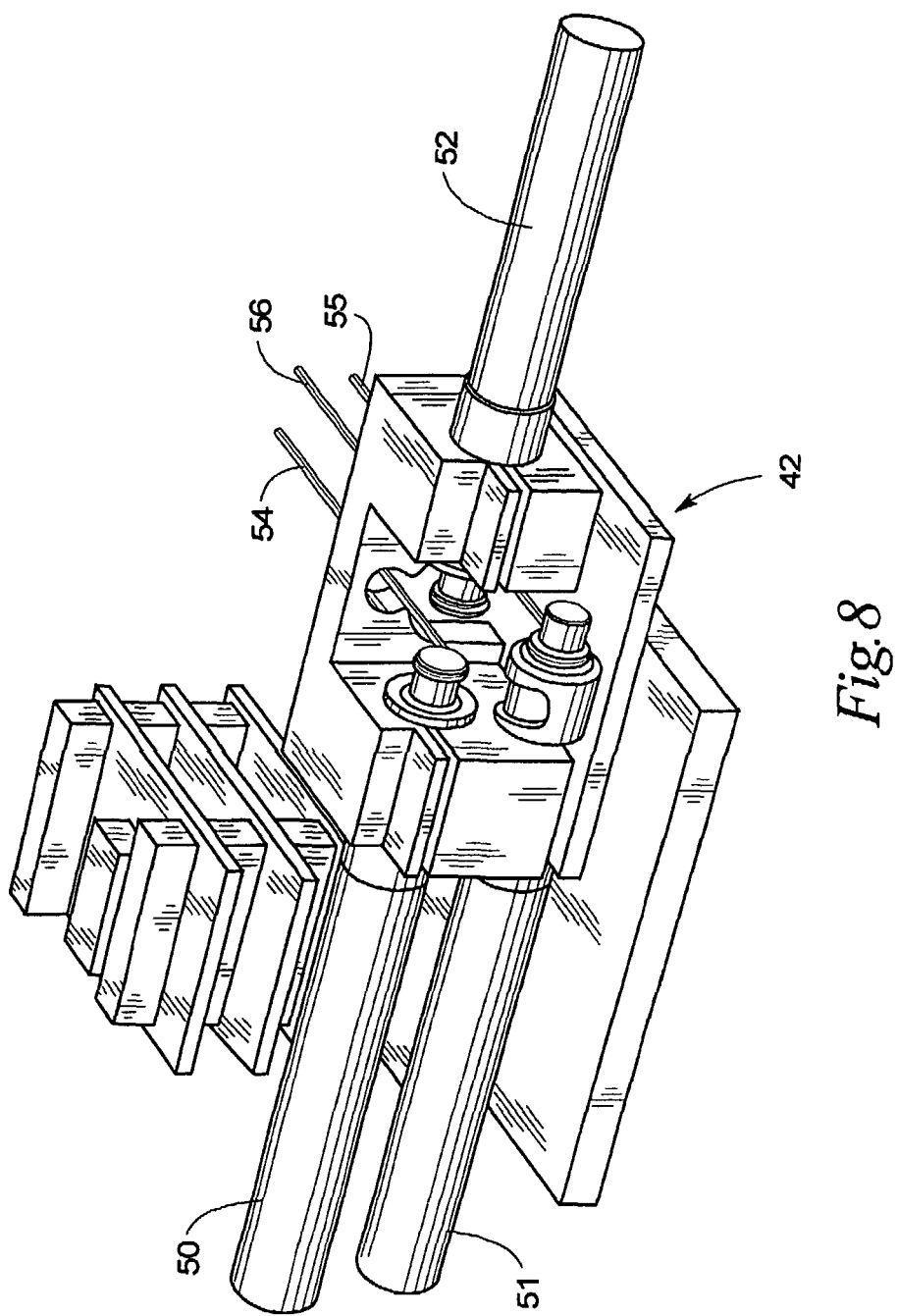
FIG. 8 illustrates devices for controlling the tension on the wires of the outer sleeve.
Figure 9:
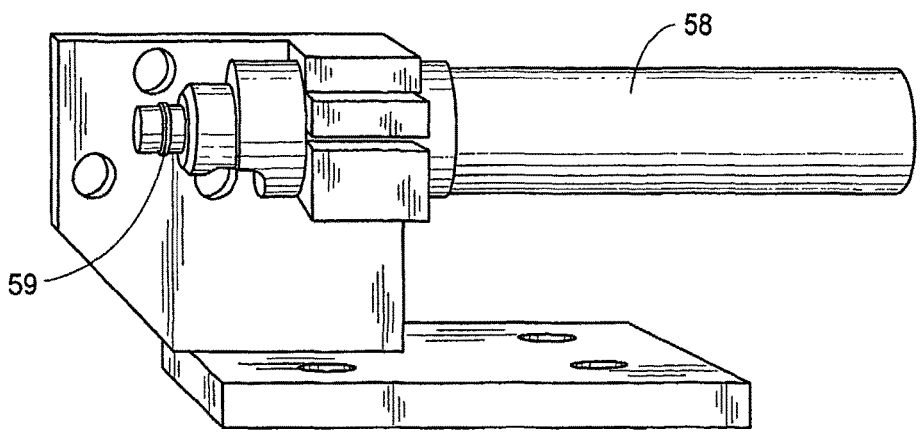
FIG. 9 illustrates a device for controlling the tension on the wire of the inner sleeve.

Each of the carts 42, 44 carries one or more motors necessary for controlling the wires of the inner core 12 and outer sleeve 14. For example, as seen in FIG. 7 and FIG. 8, the cart 42 carries motors 50, 51, 52 which control the tension on wires 54, 55, 56 of outer sleeve 14. As shown in FIG. 9, second cart 44 has a motor 58 for controlling the tension on wire 59 of the inner core 12. Each of the motors 50, 51, 52 and 58 may be provided with shaft encoders (not shown) used for position control as is known. If the inner core 12 were to also be steerable, it too would require three motors.

For the 12 mm diameter HARP 10, the feeder's 16 dimensions are 400 mm (long) by 100 mm (width/height), while the HARP is 300 mm long. The 12 mm prototype HARP 10 is inserted into a protective plastic bag to achieve sterility. However, the device can be constructed out of inexpensive ABS plastic rendering the device disposable.

We selected motors to handle the "worst case" configuration for the device, i.e. when the motors tensioning the wires have to exert the most torque. The "worst case" configuration is when the HARP 10 is stretched out in a cantilever position, the outer sleeve 14 is limp, and the inner core 12 supports its own weight as well as the weight of the outer sleeve 14.

Figure 10A:
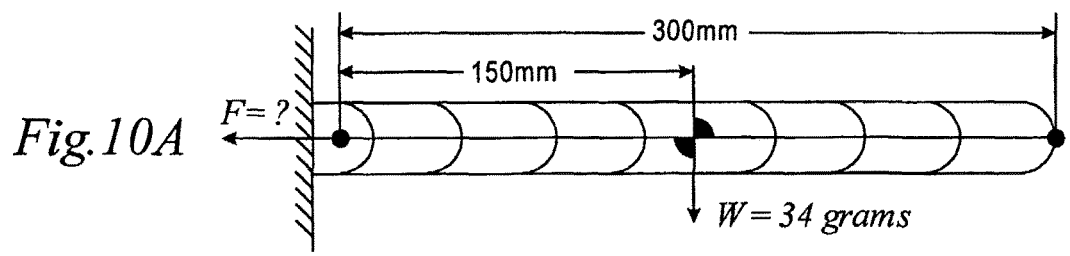
FIGS. 10A-10C illustrate a schematic of extreme cantilever configuration for a worst case configuration (A), a simplified model (B), and a free body diagram (C) for the worst case configuration.
Figure 10B:
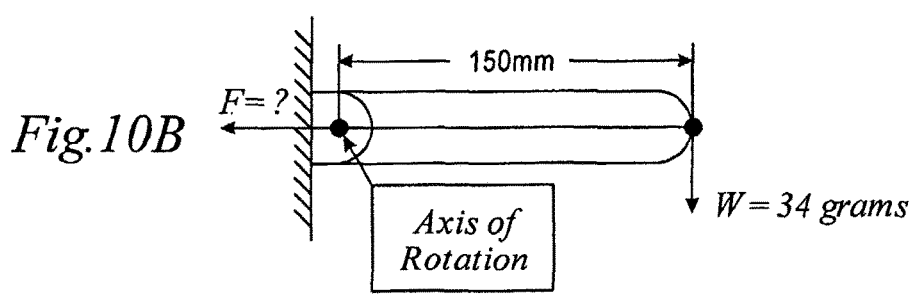
Figure 10C:
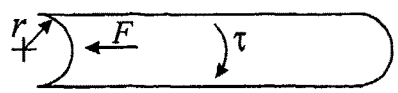

To estimate the axial force needed to be applied by the wire 59 of the inner core 12 to support this configuration, we use a simplified model of this extreme configuration. The simplified model is shown in FIGS. 10A-10C where we approximate the system parameters as follows: outer sleeve cylinder weight as 1.5 grams, inner sleeve cylinder weight as 0.5 grams, and the number of cylinders in each is seventeen. Therefore, the total weight of the device is thirty-four grams and its total length is 300 mm. Finally, the outer diameter of the outer sleeve 14 is 12 mm and the outer diameter of the inner core 12 is 6 mm. The choice of 12 mm is based on available ports and the 6 mm follows by design.

The weight of the device is simplified to a point mass at the center of gravity of the device. The largest torque is exerted on the area between the two proximal cylinders of the HARP 10. Therefore we developed a simplified model to include only one long cylinder that is in contact with the proximal cylinder. The wire of the inner core is applied with an axial force, F, at the center of the HARP 10. A free body diagram of the simplified model is shown in FIG. 10C.

The approximated relation between the force F and the torque τ applied on a circular surface with radius r and friction coefficient μ is shown in equation (1).

$$\tau = \mu \cdot F \cdot r \Rightarrow F = \frac{\tau}{\mu \cdot r} = \frac{50N \cdot mm}{\mu \cdot 3\ mm} \approx \frac{17N}{\mu} \quad (1)$$

It is clear from equation (1) that the friction coefficient is an important design criteria. When the friction between cylinders is low, the pulling force that is needed to withstand the mechanism's own weight is enormous. To find the accurate friction coefficient between cylinders some empirical tests were needed.

Three different materials were tested: Aluminum T6061-T6, Garolite® G11/FR5 and Garolite® G10/FR4. The aluminum and Garolite® G11/FR5 had a friction coefficient of approximately 0.2-0.3, but after a few minutes of being rotated under load, the contact surface was polished and smoothed out, and the friction coefficient dropped dramatically making these materials unfit for our design. The Garolite® G10/FR4, which is a high pressure laminated glass reinforced epoxy, has a very high friction coefficient (approximately 0.5) and was durable to polishing. This material is also MRI compatible.

Based on these tests, we decided to use the Garolite® G10/FR4. This material enabled the use of reasonable pulling force of the wire (approximately 35-40 N) to hold the weight of the entire device in the extreme configuration described above. Furthermore, this pulling force was sufficient to withstand additional torques caused by steering the distal link of the outer sleeve.

An implication of using the Garolite® G10/FR4 was the need for a non-abrasive wire. Therefore we used the Spectra® polyethylene fiber wire, with 0.030" diameter, a breaking force of 150 lbf, and a low stretch (about 3%). An additional advantage of the Spectra® wire is its very tight radius curvature that enabled the use of a small diameter pulley (4 mm diameter) making it possible to achieve a high pulling force per torque.

Figure 11:
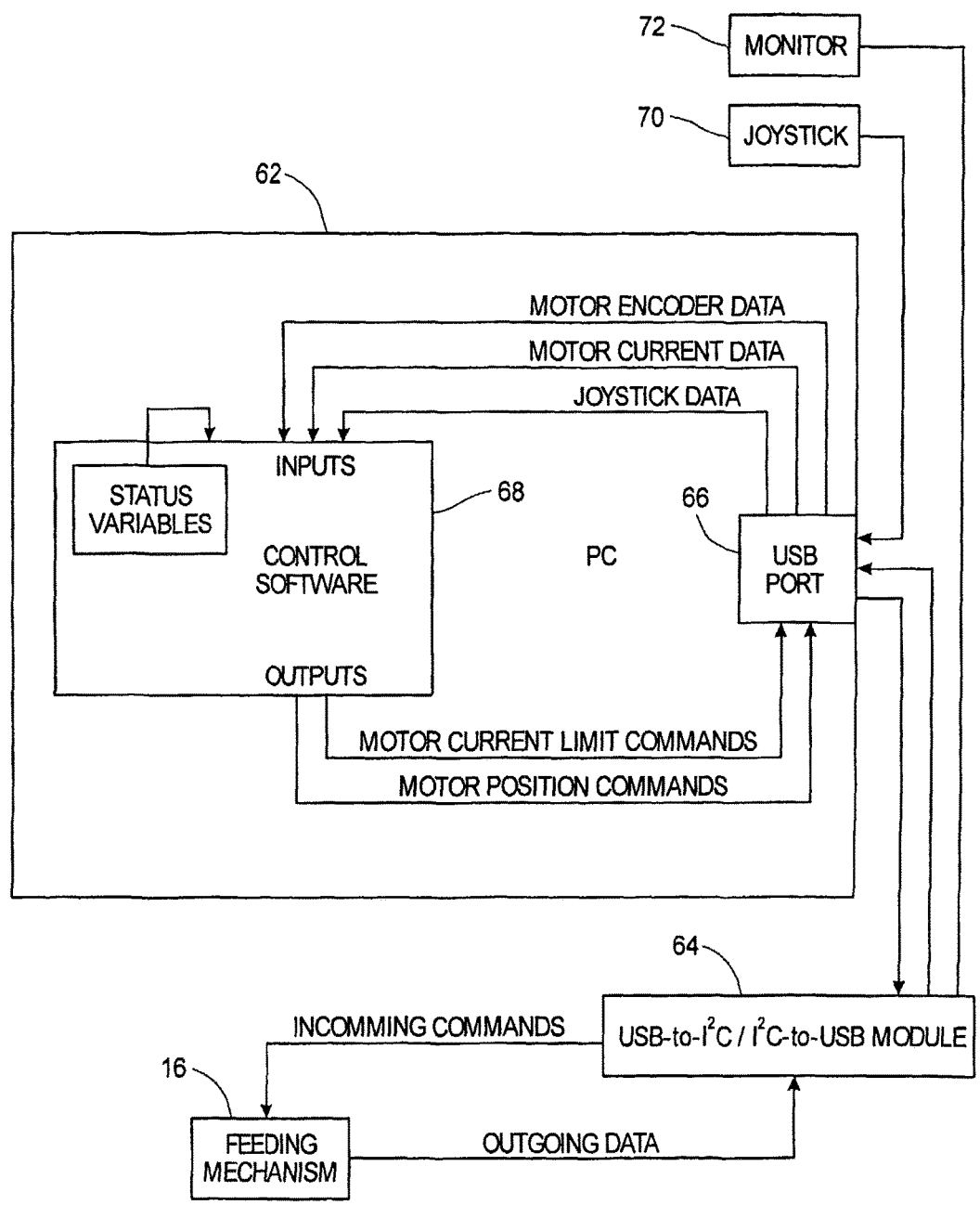
FIG. 11 is a block diagram illustrating the components of a control system and the flow of information between those components.

FIG. 11 is a block diagram illustrating the components of a control system and the flow of information between those components. The feeding mechanism 16 interfaces with a control computer 62 through a bus conversion module 64. In the present embodiment, the conversion module 64 converts USB to I²C and back again. Outgoing data from the feeding mechanism 16 is input to the module 64 for conversion to the USB and is then input to a USB port 66 on the computer 62. Incoming data to control software 68 may include motor current data and motor encoder data for each of the motors in the feeding mechanism 16. Joystick data (position data) may also be received from a joystick 70. A monitor 72 may be responsive to video data from a camera mounted on the distal end of the outer sleeve 12 and/or inner core 14 to provide visual feedback to a user regarding the position of the distal end of the HARP 10. The control software 68 may output motor current limit commands and motor position commands which are input to the feeding mechanism 16.

Figure 12:
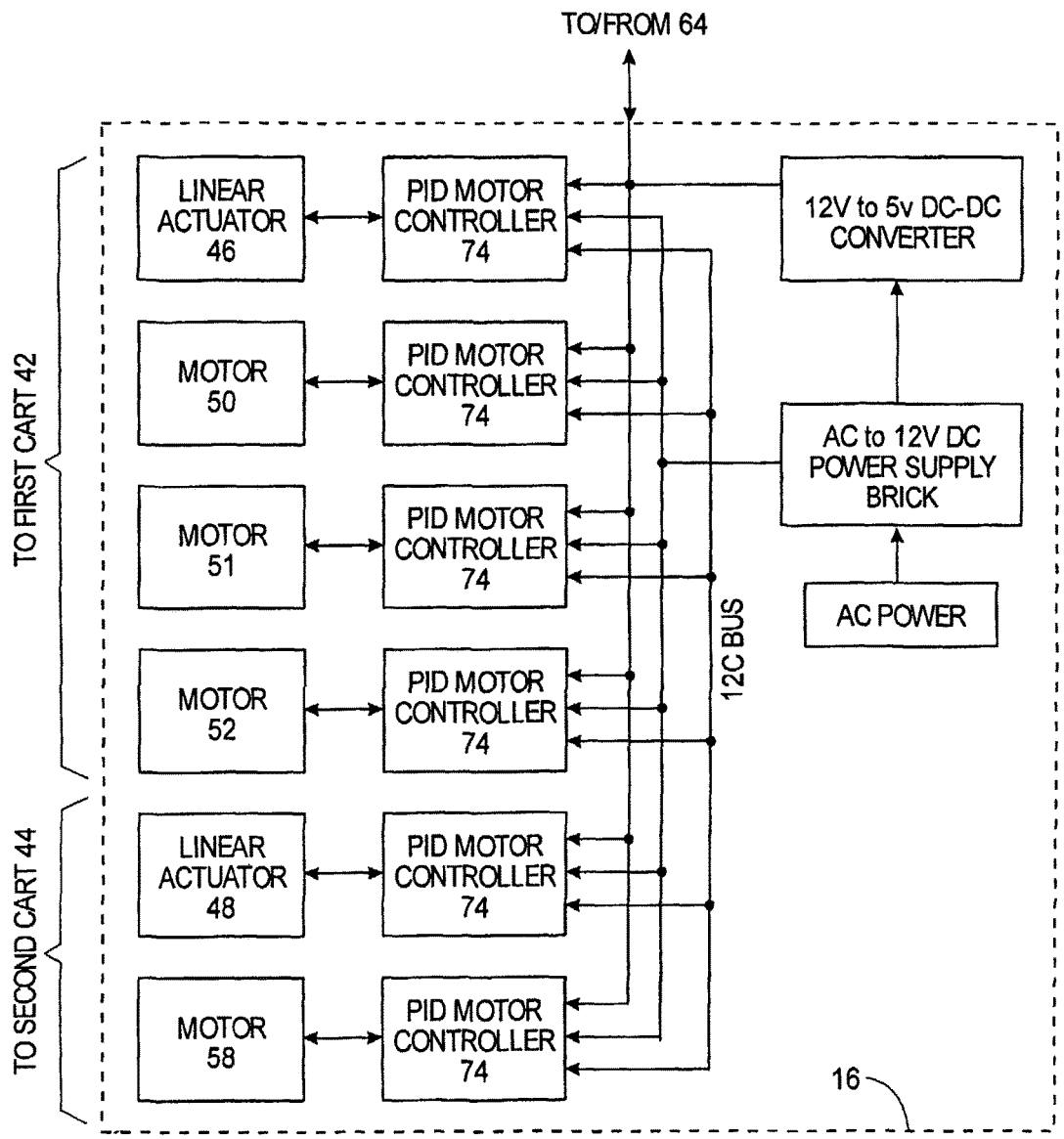
FIG. 12 is a block diagram of an exemplary electrical system for the feeding mechanism.

FIG. 12 is a block diagram of an exemplary electrical system which may be used for the feeding mechanism 16. A plurality of PID motor controllers 74 are used to control the various linear actuators 46, 48 and motors 50, 51, 52, 58. An example of one of the PID motor controllers 74 is shown in detail in FIGS. 13A, 13 B and 13C. The PID motor controller 74 is built around a PIC 18F series microcontroller 95. The motor controller 74 also features a quadrature decoder chip 96, an H-bridge chip 97, and a quad op-amp chip (TLV2374-IPW) having four amplifiers 98, 99, 100 and 101. The controller 74 also features a number of discrete components in support of these integrated circuits as well as three connectors, one connector 103 for the motor, and the other two connectors 104, 105 to create a stacking bus structure.

The quadrature chip 96 decodes the two channel encoder data from a motor encoder and outputs up and down clocks which are fed into the microcontroller 95. The microcontroller 95 uses its counter circuits to count the forward and reverse movements of the motor shaft to calculate the current position of the motor shaft.

The H-bridge chip 97 is used to drive the motor. This chip takes a PWM signal and a direction signal as input from the microcontroller 95 and switches the motor on and off according to these signals. This chip handles the higher currents and voltages required by the motor which are beyond the capabilities of the microcontroller 95 outputs.

The third chip is the quad op-amp. This chip is used entirely for motor current monitoring. One amplifier 98 is used in a non-inverting configuration with a gain of 74.2 with its output fed to one of the microcontroller's 95 analog to digital pins. A second amplifier 99 is configured as a non-inverting amplifier with a gain of 500 and is also connected to an analog to digital pin of the microcontroller 95. This higher gain gives a more precise current measurement at lower current values. A third amplifier 100 is used to control a current source which drives an LED with current proportional to the motor current. This, along with an LED which indicates the direction of motion, gives the operator a clear visual indication of what the controller 74 is doing.

The microcontroller (PIC) 95 is the heart of this board. This chip features an I²C bus peripheral which is used for communication with the host computer 62. This is a two way link used to send commands from the computer 62 to the controller 74, while status information flows back from the controller 74 to the computer 62. The commands from the computer 62 are related to position goals and current limits. The status sent back to the computer 62 includes motor electrical current measurements and motor encoder values.

The primary role of the microcontroller 95 is to rim a PID position control loop. The purpose of this PID loop is to minimize the error between the motor encoder count and a dynamically generated position goal. This position goal is generated by another component of the microcontroller program, the trajectory generation system.

The trajectory generation system of controller 74 creates goals based on a final goal supplied over the I²C bus, and a desired time-to-goal value also supplied over the I²C bus, as is known in the art. The trajectory generator uses these values to create a trapezoidal velocity profile to bring the motor to the desired final position in the specified amount of time. This working goal is updated at approximately 1 kHz, which is also the frequency of the HD loop.

Simultaneously, the microcontroller 95 is also taking readings of the motor current via the on chip analog to digital converter. These values are compared against an I²C bus supplied maximum current value, and if the measured current exceeds the desired maximum, the PWM output to the H-bridge is throttled back. This also runs at the same frequency as the PID loop.

The controller 74 is designed to allow multiple controllers 74 to be stacked by utilizing a 40 conductor board to board connector 104, 105 (FIG. 13B) on both the top and bottom of the board. Because the system uses the multi-drop I²C bus, only two connections are needed between boards in addition to power. The majority of the conductors on these stacking connectors are used for power to overcome the single pin current limitations of small connectors like these.

Motors are connected to their respective controllers 74 through a 2×5 100 mil spacing right angle header 103. This is a versatile connector which allows ribbon cable or discrete wiring to the motors. The motors used on this system were supplied with ribbon cable IDC connectors.

Figure 13A:
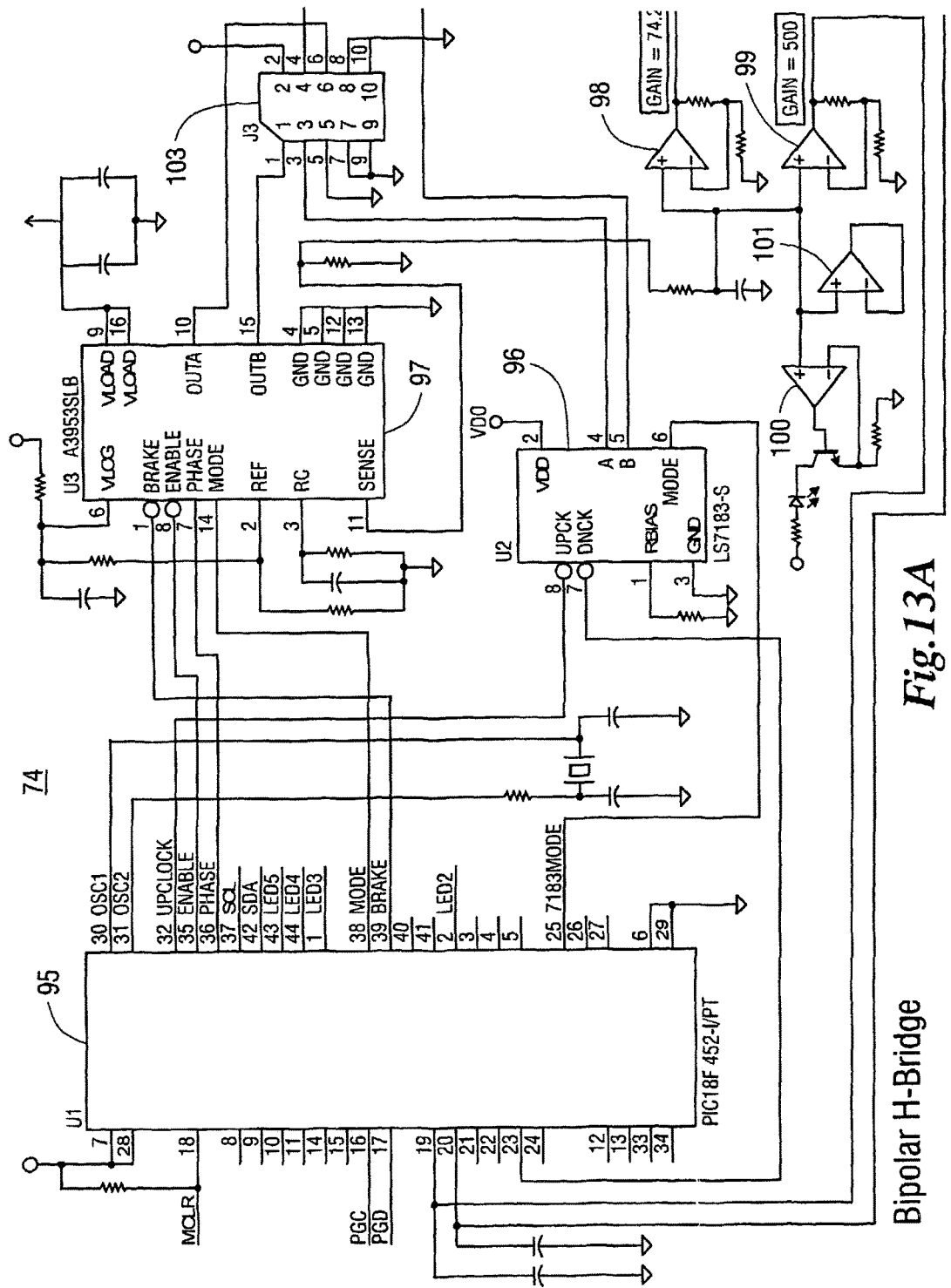
FIGS. 13A, 13B and 13C are an electrical schematic of a PID motor controller of FIG. 12.
Figure 13B:
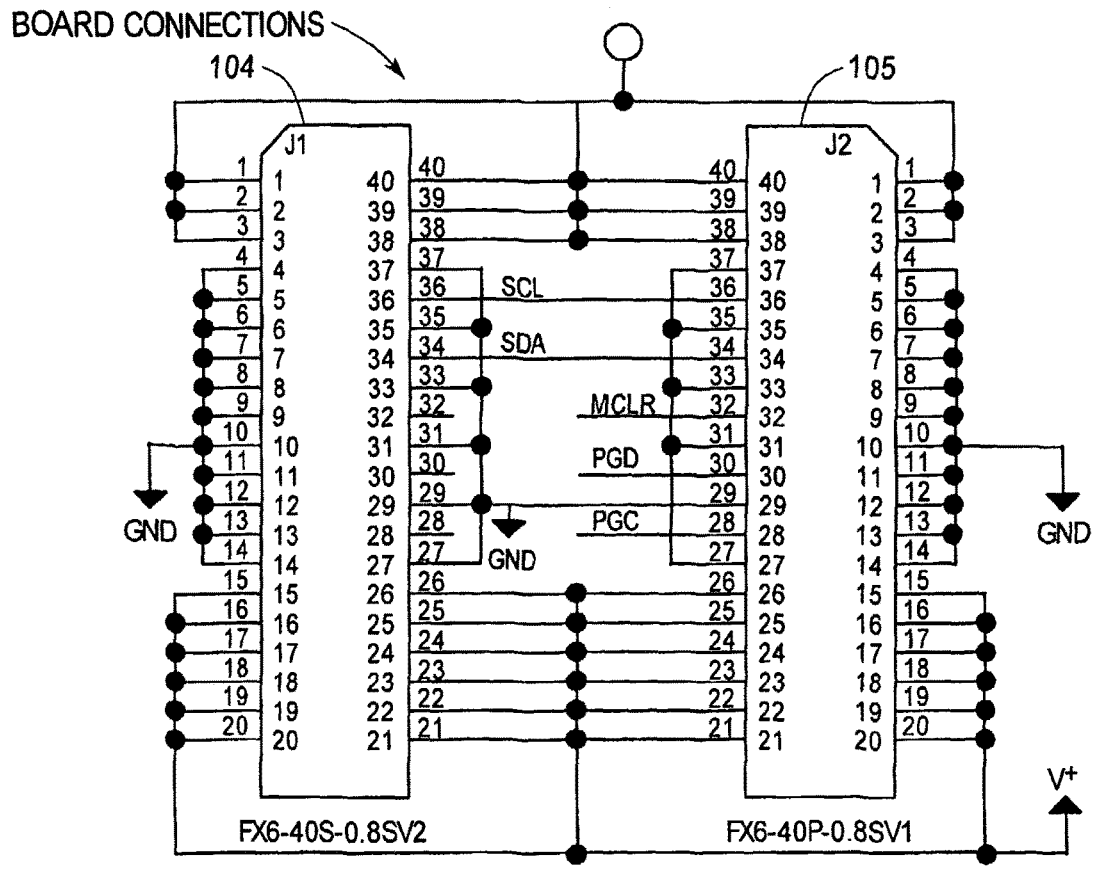
Figure 13C:
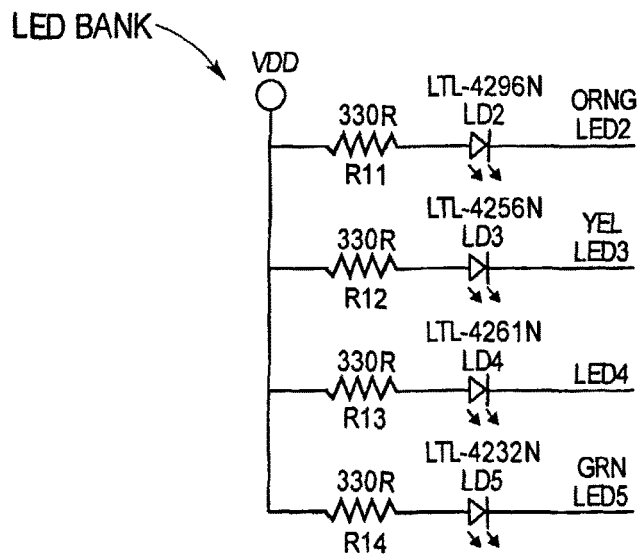

Each board also features 5 LEDs, one of which is shown in FIG. 13A and the others shown in FIG. 13C, with the others connected to the microcontroller 95 as shown in FIG. 13A. There is a red LED (closest to the stacking connector) which is controlled by the motor current. Next is a yellow LED indicating the sign of the error from the PID loop, which indicates the direction the motor's shaft is being commanded to turn. The middle LED is currently unused and is available for future use. The green LED is used as a power/boot indicator and is under software control. Finally, another red LED (near the motor connector) is toggled each time an error is detected on the I²C bus to visually indicate bus reliability.

Before the system can be used, the first mechanism 12 and the second mechanism 14 must be "homed"; that is, their relative positions must be determined. This is done by retracting both mechanisms until the linear actuators 46, 48 have reached the end of their range of travel, a condition detected by the system as an increase in actuator current. The control software 68 uses encoder information to record the positions of the first mechanism 12 and second mechanism 14, and homing is complete.

Figure 14:
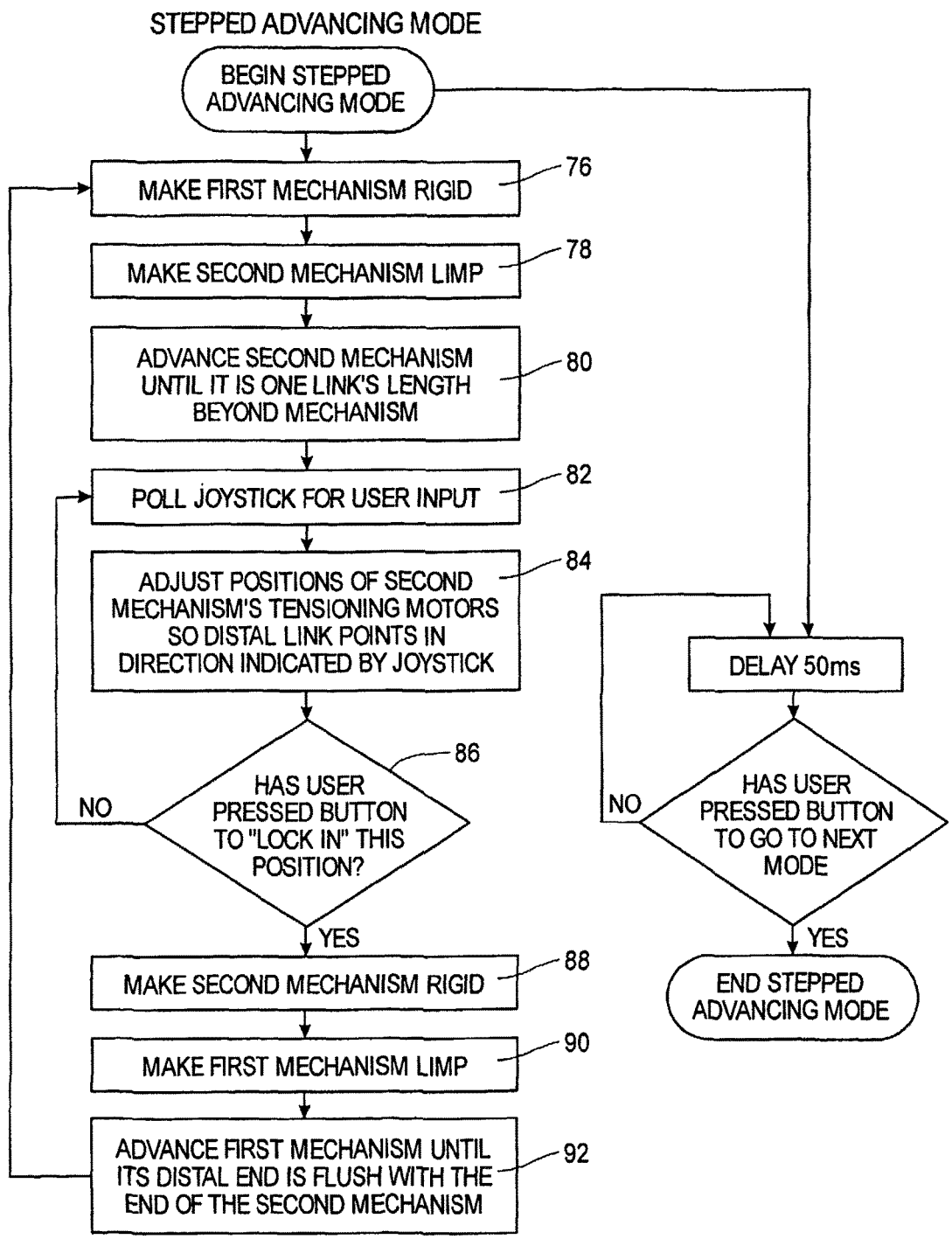
FIG. 14 is flow chart of a stepped advancing mode of operation.
Figure 15A:
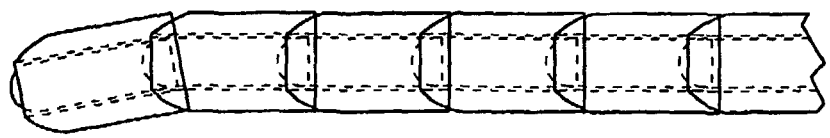
FIGS. 15A-15C illustrate a process for moving the device of the present disclosure.
Figure 15B:
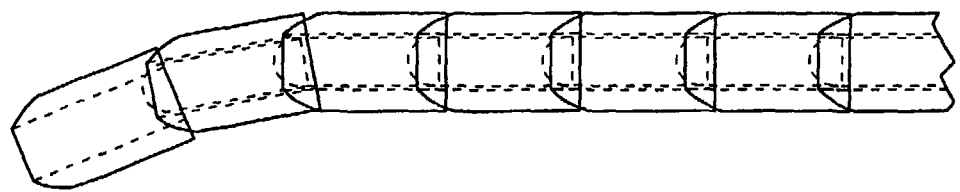

The control software then puts the system in "stepped advancing" mode which is illustrated in FIG. 14. First, the first mechanism 12 is made rigid at 76. See also FIG. 15A. That is done by driving its tensioning motor 58 in the direction opposite the tension wire's 59 pull until the motor 58 stalls at its current limit. The second mechanism 14 is made limp at 78 by driving its tensioning motors 50, 51, 52 in the direction of the tension wires' pull by a fixed number of rotations, so that the wires become slack. The second mechanism 14 is advanced at 80 (See also FIG. 15B) so that it is positioned with its distal end one link's length beyond the first mechanism's 12 end. An encoder on the linear actuator 46 that is pushing the second mechanism 14 "counts" how far the second mechanism has moved.

At this point, the software 68 is ready for user input. The software 68 monitors the position of the joystick 70 at 82, translating the two-axis data from the joystick into the three-axis coordinate system of the second mechanism 14. The positions of the shafts of the motors 50, 51, 52 controlling wires 54, 55, 56, respectively, are varied at 84 according to the translated joystick position. Once the user has steered the protruding link of the second mechanism 14 to the desired angle, the user presses a button on the joystick 70 to lock that angle in place as shown at 86. The three tensioning motors 50, 51, 52 are driven in the direction opposite the tension wires' 54, 55, 56 pull, until their current limits are reached and the motors stall at 88. This begins with the wire closest to the inside of the angle being formed, progressing after a small fixed delay to the next wire and finally the wire on the outermost part of the angle; tensioning the wires in this order preserves the user-selected angle more accurately than tensioning them simultaneously.

Figure 15C:
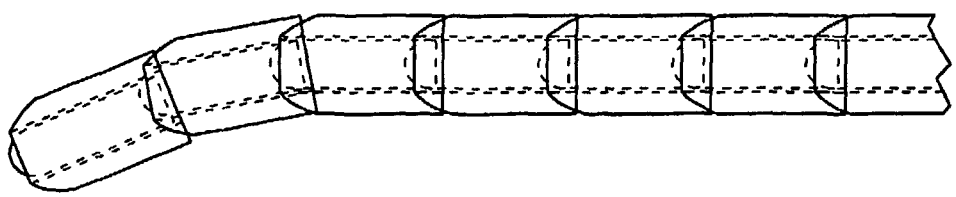

Once each of the three motors 50, 51, 52 has reached its current limit, the second mechanism 14 is rigid and the first mechanism 12 can safely be made limp as shown by 90 by driving its tensioning motor 58 a fixed number of rotations in the direction of the tension wire's 59 pull. The first mechanism 12 is then advanced by one link's length, so that its distal end is even or coextensive with the second mechanism's 14 distal end as shown by 92 and FIG. 15C. An encoder on the linear actuator 48 that pushes the first mechanism 12 is used to count how far the first mechanism 12 advances. Once in this position, the distal links of both the first mechanism 12 and the second mechanism 14 are at the same angle. The first mechanism 12 is then made rigid to preserve this angle, and the second mechanism 14 is made limp as shown by 76 and 78. In this way the process continues, steering the distal link, locking its position in place, and advancing in single-link steps until the first mechanism 12 and second mechanism 14 have been advanced to the desired length and path shape.

The description of motion in conjunction with FIG. 14 and FIGS. 15A-15C assumes that a camera, not shown, is positioned on the distal link of the second mechanism 14. Thus, the second mechanism 14 does the steering while the first mechanism 12 simply follows along. The process could of course be reversed with the camera being positioned on the first mechanism 12 such that the first mechanism 12 does the steering, while the second mechanism 14 does the following. In another embodiment, cameras could be provided on the distal ends of both the first mechanism 12 and the second mechanism 14 such that the two mechanisms "leap frog" one another. That is, rather than one of the mechanisms merely catching up with the other, after it is caught up, it can advance by one link because of its capability of being steered. The other mechanism then "catches up" and advances by one link's length because it too has the capability of steering. It is anticipated that with such a device, a desired position for the end of the HARP 10 may be obtained more quickly.

Although it is anticipated that steering may be achieved through the use of cameras, other mechanisms may be used. For example, the distal links of each of the first mechanism 12 and second mechanism 14 may be comprised of material which is visible through the use of x-rays, NMRI, or other such devices such that the HARP 10 may be steered by tracking the advance of the HARP 10 with such a device. Alternatively, a small amount of radioactive material may be placed on the distal end of each of the first mechanism 12 and second mechanism 14 such that the progress of the HARP 10 can be tracked. Control of the path and configuration of the HARP 10 may be accomplished through the use of intelligent algorithms. The present invention is not to be limited by the type of mechanism used to provide information for steering and/or guidance of the HARP 10.

Figure 16:
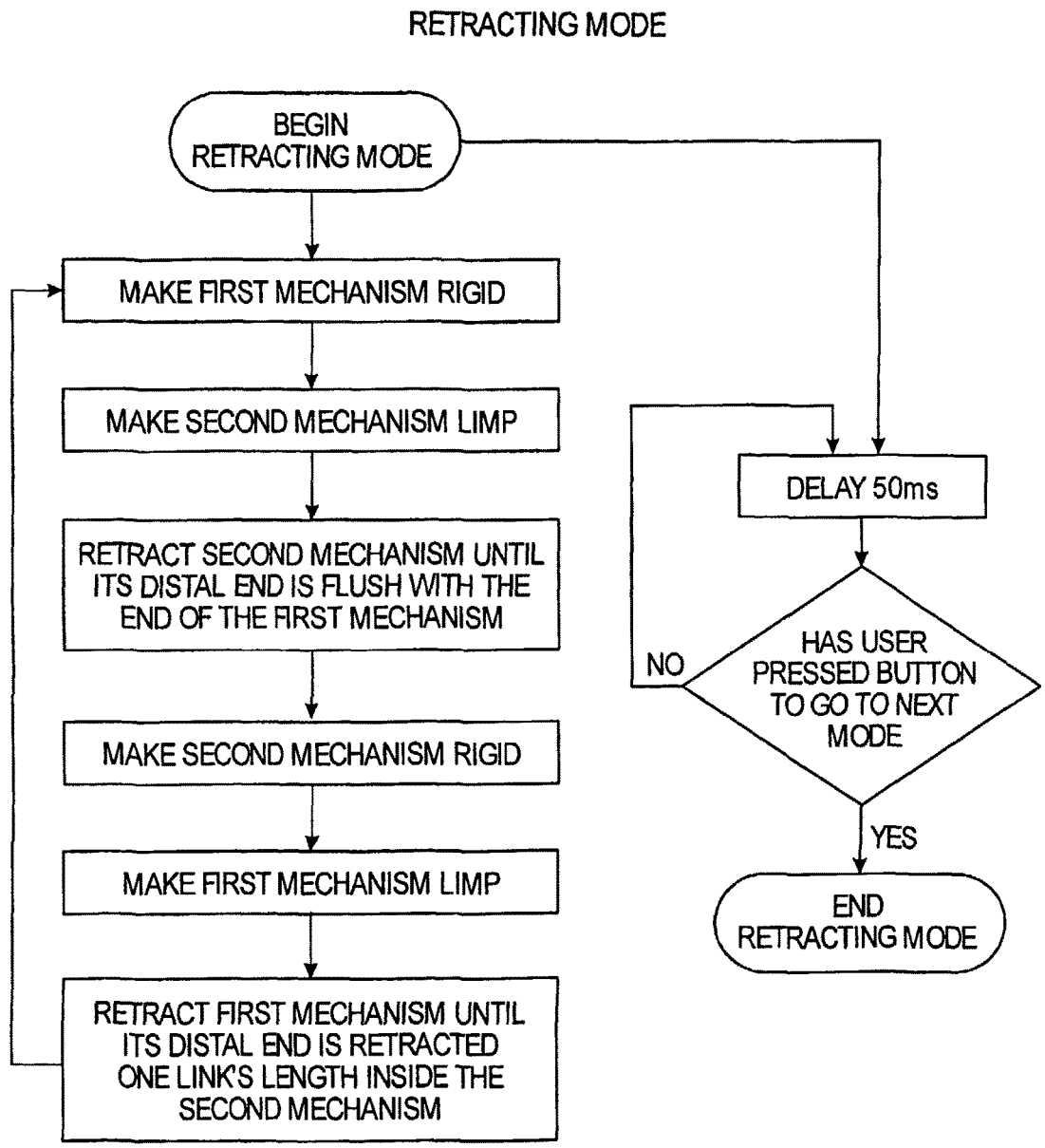
FIG. 16 is a flow chart of a process for retracting the device.

The process of retracting the mechanisms takes place in the same way as advancing does, but in reverse order, and without steering input from the user as shown in FIG. 16. Once the user has selected "Retracting" mode using the joystick 70, the second mechanism 14 is refracted so that its distal end is even with the distal end of the first mechanism 12. The second mechanism 14 is made rigid, and the first mechanism 12 is made limp. Then the first mechanism 12 is retracted by one link's length, and the first mechanism 12 is made rigid. The second mechanism 14 is made limp, and again retracted until the distal end of the second mechanism is even with the distal end of the first mechanism 12. That cycle continues until the user presses a button to stop it, or until the first mechanism 12 and second mechanism 14 reach their home positions.

Turning now to experimental results, an off-the-shelf fiber optic based camera and video camera, such as the Olympus PF14 insertion tube 1.4 mm was introduced through the open central portion of the links of an inner core 12 designed to have a 6 mm diameter opening. Another option would be to integrate the video camera into the walls of the links of the outer sleeve 14, which are currently 3 mm thick. With such a device, and as shown in FIGS. 18 and 19, we were able to navigate the pericardial space of a porcine.

The normal pericardium is a double-layered, flask-shaped sac consisting of an outer fibrous envelope and in inner serous sac that is invaginated by the heart. The pericardial cavity or sac is a continuous virtual space that lies between the two opposite layers of serous pericardium. At the pericardial reflections and at the posterior wall between the great vessels, the pericardial space is apportioned into a contiguous network of recesses and sinuses; all pericardial reflections are located basally in relation to the great vessels. Thus, there are no obstacles during intrapericardial navigation along the anterior ventricular surface of the heart. There are three sinuses in the pericardial space: the superior sinus (also referred to as superior aortic recess), the transverse sinus contains several recesses between the major vessels (superior aortic, inferior aortic, right pulmonary and left pulmonary recess). The inferior aortic recess allows access to the epicardial aspect of the noncoronary and right coronary aortic cusps. The oblique sinus extends behind the atria, particularly the left atrium, in the region between the four pulmonary veins. There are five recesses of the pericardial cavity: superior aortic (SAR), inferior aortic (AR), postcaval (PCR), left pulmonary (LPVR) and right pulmonary (RPVR).

Figure 18:
FIGS. 18 and 19 illustrate an embodiment of the present disclosure having an onboard camera mounted on the end thereof and used for visualization of internal organs.
Figure 19:

As shown in FIGS. 18 and 19, we were able to explore the oblique sinus and visualize the posterior atrium, explore the transverse sinus with entry from the right and from the left with visualization of the left atrial appendage and explore all five recesses (SAR, IAR, PCR, LPVR and RPVR). Thus, the device and method of the present invention allow for various types of endoscopy or visualization of internal organs (or parts) or intracavity spaces from an on-board camera (or lens and light pipe) mounted on an articulated probe. It is the real time images provided by the on-board camera that allow teleoperation, i.e. remote controlled, 3D guidance in real time.

Figure 20:
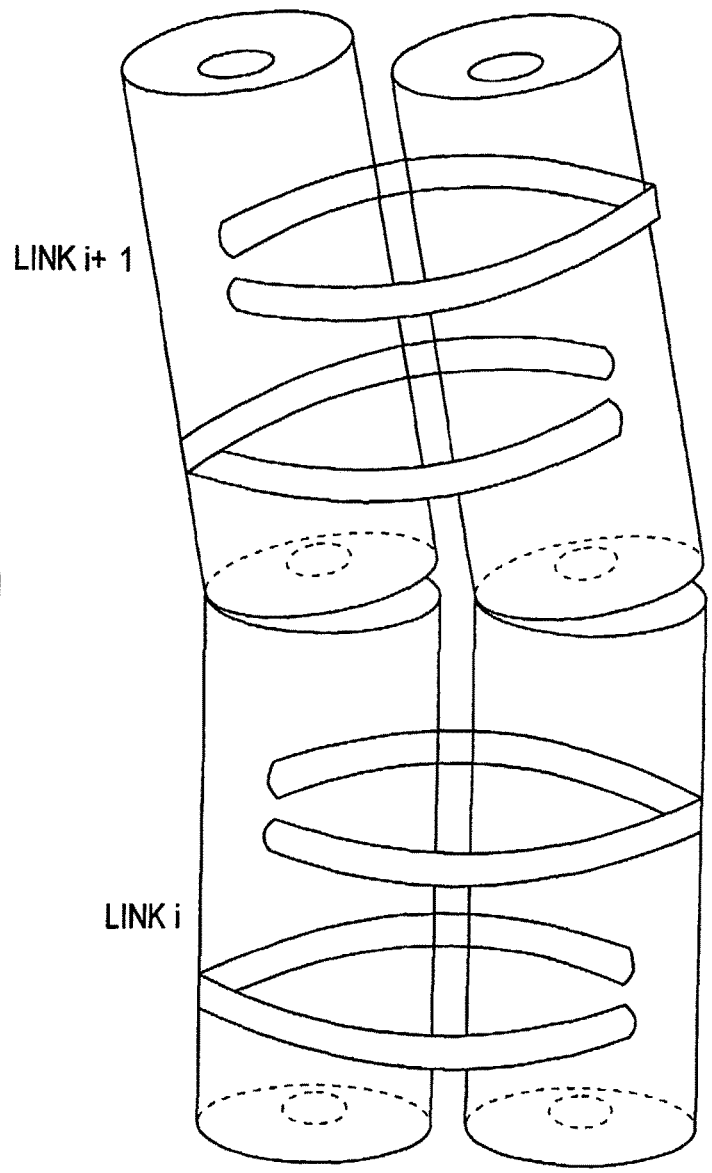
FIG. 20 illustrates another embodiment of the device of the present disclosure.

While the present invention has been described in connection with preferred embodiments thereof, those of ordinary skill in the art will recognize that many modifications, variations and substitutions are possible. For example, as shown in FIG. 20, the first mechanism 12 and the second mechanism 14 are shown in a spaced relationship, i.e. not one within the other. In such an embodiment, one or both of the mechanisms may have members for maintaining the spaced relationship as the device 10 moves. Accordingly, the present invention is not intended to be limited by the disclosed embodiments but rather is limited only by the scope of the following claims.

What is claimed is:

1. A method of operating a highly articulated probe, the method comprising:
   adjusting a position of the highly articulated probe having a first mechanism and a second mechanism, wherein the second mechanism is configured to surround at least a portion of the first mechanism, and wherein the first mechanism starts in a rigid state and the second mechanism starts in a limp state, by:
   advancing the second mechanism by advancing a first cart to which the second mechanism is responsive a predetermined distance, wherein the first cart carries a plurality of first tensioning mechanisms,
   making the second mechanism rigid using the plurality of first tensioning mechanisms by adjusting a position of the plurality of first tensioning mechanisms to control a plurality of wires, wherein each of the plurality of wires is connected to at least one of the plurality of first tensioning mechanisms and the second mechanism, and
   making the first mechanism limp using a second tensioning mechanism carried by a second cart by adjusting a position of the second tensioning mechanism to control one or more wires connected to the second tensioning mechanism and the first mechanism,
   wherein at least one of the first mechanism and second mechanism is steerable when in the limp state,
   wherein the first cart and the second cart are independently driven by different actuators.

2. The method of claim 1 wherein advancing the second mechanism comprises advancing the second mechanism beyond a distal end of the first mechanism.

3. The method of claim 1 additionally comprising: generating images from a device mounted on the end of said probe as said probe moves within a three dimensional space; and using the images to control the movement of said probe.

4. The method of claim 3 wherein said generating images comprises generating images with one of a camera and a lens.

5. The method of claim 1 additionally comprising: generating images of a three dimensional space, said images including at least the position of a distal end of said probe; and using the images to control the movement of said probe.

6. The method of claim 5 wherein said images are generated using one of MRI, sound, ultrasound, and radiation.

7. The method of claim 5 wherein said using the images to control the movement of said probe is carried out in real time.

8. The method of claim 5 wherein the space is the pericardium, said method additionally comprising making an incision below the xiphoid process and inserting said probe into said incision.

9. The method of claim 5 additionally comprising performing an examination of a bodily organ, body part, intracavity space or natural body pathway during movement of said probe.

10. The method of claim 1, wherein advancing the first cart to which the second mechanism is responsive a predetermined distance comprises advancing, by a first actuator, the first cart.

11. The method of claim 10, wherein the first actuator comprises a motor.

12. The method of claim 1, wherein one or more of the plurality of first tensioning mechanisms or the second tensioning mechanism comprises a motor.

13. The method of claim 1, further comprising:
   advancing the first mechanism by advancing the second cart to which the first mechanism is responsive;
   making the first mechanism rigid using the second tensioning mechanism by adjusting a position of the second tensioning mechanism to control one or more wires connected to the second tensioning mechanism and the first mechanism; and
   making the second mechanism limp using the plurality of first tensioning mechanisms.

14. The method of claim 13, wherein advancing the second cart to which the first mechanism is responsive comprises advancing, by a second actuator, the second cart.

15. The method of claim 1, wherein:
   the first cart is carried in a first fixed tray, and
   the second cart is carried in a second fixed tray.

16. A method of operating a highly articulated probe, the method comprising:
   adjusting a position of the highly articulated probe having a first mechanism and a second mechanism, wherein the second mechanism is configured to surround at least a portion of the first mechanism, and wherein the first mechanism starts in a limp state and the second mechanism starts in a rigid state, by:
   advancing the first mechanism by advancing a first cart to which first mechanism is responsive a predetermined distance, wherein the first cart carries a first tensioning mechanism,
   making the first mechanism rigid using the first tensioning mechanism by adjusting a position of the first tensioning mechanism to control one or more wires connected to the first tensioning mechanism and the first mechanism, and
   making the second mechanism limp using a plurality of second tensioning mechanisms carried by a second cart by adjusting a position of the plurality of second tensioning mechanisms to control a plurality of wires connected to the second tensioning mechanism and the second mechanism,
   wherein at least one of the first mechanism and second mechanism is steerable when in the limp state,
   wherein the first cart and the second cart are independently driven by different actuators.

17. The method of claim 16 wherein advancing the first mechanism comprises advancing the first mechanism beyond a distal end of the second mechanism.

18. The method of claim 16, further comprising:
   advancing the second mechanism by advancing the second cart to which the second mechanism is responsive;
   making the second mechanism rigid using the second tensioning mechanism by adjusting a position of the plurality of second tensioning mechanisms to control the plurality of wires, wherein each of the plurality of wires is connected to at least one of the plurality of second tensioning mechanism and the second mechanism; and
   making the first mechanism limp using the first tensioning mechanism.

19. The method of claim 16, wherein:
the first cart is carried in a first fixed tray, and
the second cart is carried in a second fixed tray.

* * * * *